(12) United States Patent
Thatcher et al.

(10) Patent No.: US 11,175,205 B2
(45) Date of Patent: Nov. 16, 2021

(54) SAMPLE PREPARATION FOR DIFFICULT SAMPLE TYPES

(71) Applicant: BioFire Diagnostics, LLC, Salt Lake City, UT (US)

(72) Inventors: Stephanie Anne Thatcher, Salt Lake City, UT (US); Jeremy Paul Green, Salt Lake City, UT (US); Erik Wong Huynh, West Jordan, UT (US); Andrew Clinton Hemmert, Murray, UT (US); Jesse Linton Montgomery, Centerville, UT (US); Robert John Crisp, Cottonwood Heights, UT (US); Kendall A. Rasband, Salt Lake City, UT (US); Elizabeth Mary Ott Crowther, Sandy, UT (US); Cheryl Lynn Baird, Salt Lake City, UT (US)

(73) Assignee: BioFire Diagnostics, LLC, Salt Lake City, UT (US)

( * ) Notice: Subject to any disclaimer, the term of this patent is extended or adjusted under 35 U.S.C. 154(b) by 316 days.

(21) Appl. No.: 15/340,612

(22) Filed: Nov. 1, 2016

(65) Prior Publication Data

US 2017/0122851 A1 May 4, 2017

Related U.S. Application Data

(60) Provisional application No. 62/249,592, filed on Nov. 2, 2015.

(51) Int. Cl.
*C12Q 1/68* (2018.01)
*G01N 1/40* (2006.01)
*C12N 15/10* (2006.01)
*C12Q 1/6806* (2018.01)
*G01N 1/02* (2006.01)

(52) U.S. Cl.
CPC ....... *G01N 1/4077* (2013.01); *C12N 15/1006* (2013.01); *C12Q 1/6806* (2013.01); *G01N 1/02* (2013.01); *G01N 2001/028* (2013.01); *G01N 2001/4088* (2013.01)

(58) Field of Classification Search
None
See application file for complete search history.

(56) References Cited

U.S. PATENT DOCUMENTS

| | | | |
|---|---|---|---|
| 6,645,758 B1 | 11/2003 | Schnipelsky et al. | |
| 6,780,617 B2 | 8/2004 | Chen | |
| 7,387,887 B2 | 6/2008 | Wittwer et al. | |
| 8,394,608 B2 | 3/2013 | Ririe et al. | |
| 8,652,782 B2* | 2/2014 | Fischer | C12Q 1/6806 435/6.12 |
| 8,895,295 B2 | 11/2014 | Ririe et al. | |
| 9,012,208 B2* | 4/2015 | Selden | B01L 3/502715 435/287.2 |
| 9,808,798 B2* | 11/2017 | Ismagilov | B01L 3/5027 |
| 2004/0157219 A1 | 8/2004 | Lou et al. | |
| 2011/0217694 A1* | 9/2011 | Buzatu | C12Q 1/06 435/5 |
| 2012/0024788 A1 | 2/2012 | Kelso et al. | |
| 2014/0030703 A1 | 1/2014 | Fischer et al. | |
| 2014/0038272 A1 | 2/2014 | Ririe | |
| 2014/0073517 A1 | 3/2014 | Zhou et al. | |
| 2014/0212882 A1 | 7/2014 | Handique et al. | |
| 2014/0275510 A1 | 9/2014 | Gundling | |
| 2014/0283945 A1 | 9/2014 | Jones et al. | |
| 2015/0064729 A1 | 3/2015 | Nonaka et al. | |
| 2015/0353919 A1 | 12/2015 | Mielke et al. | |

FOREIGN PATENT DOCUMENTS

| | | | | |
|---|---|---|---|---|
| CN | 104246505 A | | 12/2014 | |
| JP | 2004245831 | * | 9/2004 | ............... G01N 1/10 |
| JP | 2004245831 A | | 9/2004 | |
| JP | 2014503068 A | | 2/2014 | |
| JP | 2014533176 A | | 12/2014 | |
| WO | 03016552 | | 2/2003 | |
| WO | 03070898 | | 8/2003 | |
| WO | 2012027302 A2 | | 3/2012 | |
| WO | 2012050787 A1 | | 4/2012 | |
| WO | 2012093350 A1 | | 7/2012 | |
| WO | 2013074391 A1 | | 5/2013 | |

OTHER PUBLICATIONS

Falsey et al. (Journal of Clinical Microbiology, 2012, 50(8):2835) (Year: 2012).*
Barache et al. (J of Clin Microbiol, 2014, 52(10):3590-3596) (Year: 2014).*
Panpradistetal. (PLoS One, Sep. 2014, vol. 9, issue 9, e105786, p. 1-11, Supplemental Figures 1-9 and Table 1-2 attached) (Year: 2014).*
Patel et al. (J Clin Microbiol, 2011, p. 2266-2268) (Year: 2011).*
Davis et al. (Rheol Acta, 1971, vol. 10, p. 28-35) (Year: 1971).*
Manual translation of JP2004245831, Sep. 2004.*
International Search Report and the Written Opinion of the International Searching Authority corresponding to International Patent Application No. PCT/US2016/059928 (20 pages) (dated Mar. 2, 2017).
International Preliminary Report on Patentability corresponding to International Patent Application No. PCT/US2016/059928 (20 pages) (dated Feb. 5, 2018).
World Health Organization "WHO guidelines for the collection of human specimens for laboratory diagnosis of avian influenza infection" https://www.who.int/influenza/human_animal_interface/virology_laboratories_and_vaccines/guidelines_collection_h5n1_humans/en/ (3 pages) (Jan. 12, 2005).
Extended European Search Report corresponding to European Patent Application No. 20203395.7 (7 pages) (dated Feb. 5, 2021).

* cited by examiner

*Primary Examiner* — Stephanie K Mummert
(74) *Attorney, Agent, or Firm* — Myers Bigel, P.A.

(57) ABSTRACT

Devices and methods are provided for collecting and handling difficult sample types.

21 Claims, 8 Drawing Sheets

SAMPLE PREPARATION FOR DIFFICULT SAMPLE TYPES

STATEMENT OF PRIORITY

This application claims the benefit, under 35 U.S.C. § 119(e), of U.S. Provisional Application Ser. No. 62/249,592, filed Nov. 2, 2015, the entire contents of which are incorporated by reference herein.

BACKGROUND

1. Technical Field

Embodiments of the present disclosure relate generally to methods and devices for extracting nucleic acids from a sample.

2. Background

In the United States, Canada, and Western Europe infectious disease accounts for approximately 7% of human mortality, while in developing regions infectious disease accounts for over 40% of human mortality. Infectious diseases lead to a variety of clinical manifestations. Among common overt manifestations are fever, pneumonia, meningitis, diarrhea, and diarrhea containing blood. While the physical manifestations suggest some pathogens and eliminate others as the etiological agent, a variety of potential causative agents remain, and clear diagnosis often requires a variety of assays be performed. Traditional microbiology techniques for diagnosing pathogens can take days or weeks, often delaying a proper course of treatment.

In recent years, the polymerase chain reaction (PCR) has become a method of choice for rapid diagnosis of infectious agents. PCR can be a rapid, sensitive, and specific tool to diagnose infectious disease. A challenge to using PCR as a primary means of diagnosis is the variety of possible causative organisms or viruses and the low levels of organism or virus present in some pathological specimens. It is often impractical to run large panels of PCR assays, one for each possible causative organism or viruses, most of which are expected to be negative. The problem is exacerbated when pathogen nucleic acid is at low concentration and requires a large volume of sample to gather adequate reaction templates. In some cases there is inadequate sample to assay for all possible etiological agents. A solution is to run "multiplex PCR" wherein the sample is concurrently assayed for multiple targets in a single reaction. While multiplex PCR has proved to be valuable in some systems, shortcomings exist concerning robustness of high level multiplex reactions and difficulties for clear analysis of multiple products. To solve these problems, the assay may be subsequently divided into multiple secondary PCRs. Nesting secondary reactions within the primary product increases robustness. Closed systems such as the FilmArray® (BioFire Diagnostics, LLC, Salt Lake City, Utah) reduce handling, thereby diminishing contamination risk.

Sample preparation is often a balance between harsh extraction and lysing conditions for releasing nucleic acids from tougher materials such as spores and paraffin preserved samples, and gentler lysing conditions that may minimize nucleic acid degradation, particularly in contaminants that lyse more easily and have longer chromosomes. It would be desirable to be able to extract nucleic acids from tougher materials without degrading other nucleic acids that may be present in the sample.

In addition, certain sample types can be difficult to handle. It can be difficult to introduce a solid, semi-solid, or viscous sample to a biological processing system. Sample types such as sputum are difficult to pipette and measure, and often require pretreatment for a period of time prior to sample processing, illustratively with heat or dithiothreitol, to reduce viscosity and help break up the sample matrix. In addition to sputum, other difficult biological samples include but are not limited to mucus, BAL, and other respiratory sample types, stool, tissue, tissue homogenate, ground tissue, paraffin treated formalin embedded tissue, bone, bone homogenate, eschars, puss, synovial fluid, lymph node aspirates, and stomach washings. Environmental samples, illustratively soil, surfaces, powders or food, are often solid or semi-solid and may also present challenges. Moreover, extensive handling during sample pre-treatment can lead to cross-contamination, can be time consuming, and it often dilutes the sample, often leading to decreased sensitivity.

The present invention addresses various issues relating to preparation of a sample prior to further testing, for example for purification of nucleic acids from a sample, for biological analysis.

SUMMARY OF THE INVENTION

In one aspect of the present disclosure, a sample collection method is provided, the method comprising collecting a sample comprising a biological or environmental substance using a swab, placing the swab with the collected sample in a sample buffer, and filtering the sample. In various illustrative embodiments, the sample buffer may include a protease or a detergent and the sample may be collected and transferred to the sample buffer using a flocked swab.

In another aspect, a sample collection method is provided, the method comprising collecting a sample comprising a biological or environmental substance, and placing the sample in a sample buffer wherein the sample buffer comprises a detergent in an amount of at least 10% by volume of the sample buffer. Illustrative embodiments may include drawing the sample through a filter.

In one more aspect, a sample collection method is provided, the method comprising collecting a sample comprising a biological or environmental substance by contacting the sample with a material that preferentially collects and releases the organism over sample matrix, and placing the material with the collected sample in a sample buffer. Illustratively, the material is a hydrophilic material or adsorbent material. In one embodiment, a fixed amount of the material reproducibly absorbs and releases an amount of the sample within a four-fold range.

In another aspect of the disclosure a cannulated vial is provided, the cannulated vial comprising a vial body having a top surface at one end, a bottom surface at an opposite end, and exterior wall therebetween defining an interior vial volume, the top surface having an opening, a cannula extending from the bottom surface and having a first end, a second end and an outer surface therebetween defining a cannula volume, the first end in fluid communication with the interior vial volume, and a filter disposed between the vial body and the cannula, and an additive provided in the cannulated vial.

In yet another aspect of the disclosure, a sample container is provided, the sample container comprising an opening configured to receive a sample, a body configured to hold a fluid, an opening configured to allow the fluid to exit, a filter disposed between the body and the exit, and an additive provided for treating the sample. Illustratively, the additive may be provided dried in the sample container. Illustrative additives include proteases, DNAses, DNAse inhibitors, RNAses, RNAse inhibitors, and lysozymes.

In still another aspect of the disclosure, a method of introducing an additive to a system is provided, the method comprising obtaining the sample container as described above, the sample container holding the fluid, introducing the sample through the opening into the fluid, drawing the fluid through the filter and out the exit.

In one more aspect, methods of amplifying nucleic acids from a direct blood sample are provided, the methods comprising adding the direct blood sample to a sample buffer, bead beating the sample buffer, extracting the nucleic acids from the sample buffer, and amplifying the nucleic acids. Illustratively, such methods may be performed in a closed sample vessel. In another illustrative method, the steps are performed without one or more of centrifugation, ethanol precipitation, and DNA digestion.

Additional features and advantages of the embodiments of the invention will be set forth in the description which follows or may be learned by the practice of such embodiments. The features and advantages of such embodiments may be realized and obtained by means of the instruments and combinations particularly pointed out in the appended claims. These and other features will become more fully apparent from the following description and appended claims, or may be learned by the practice of such embodiments as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Figure 1:
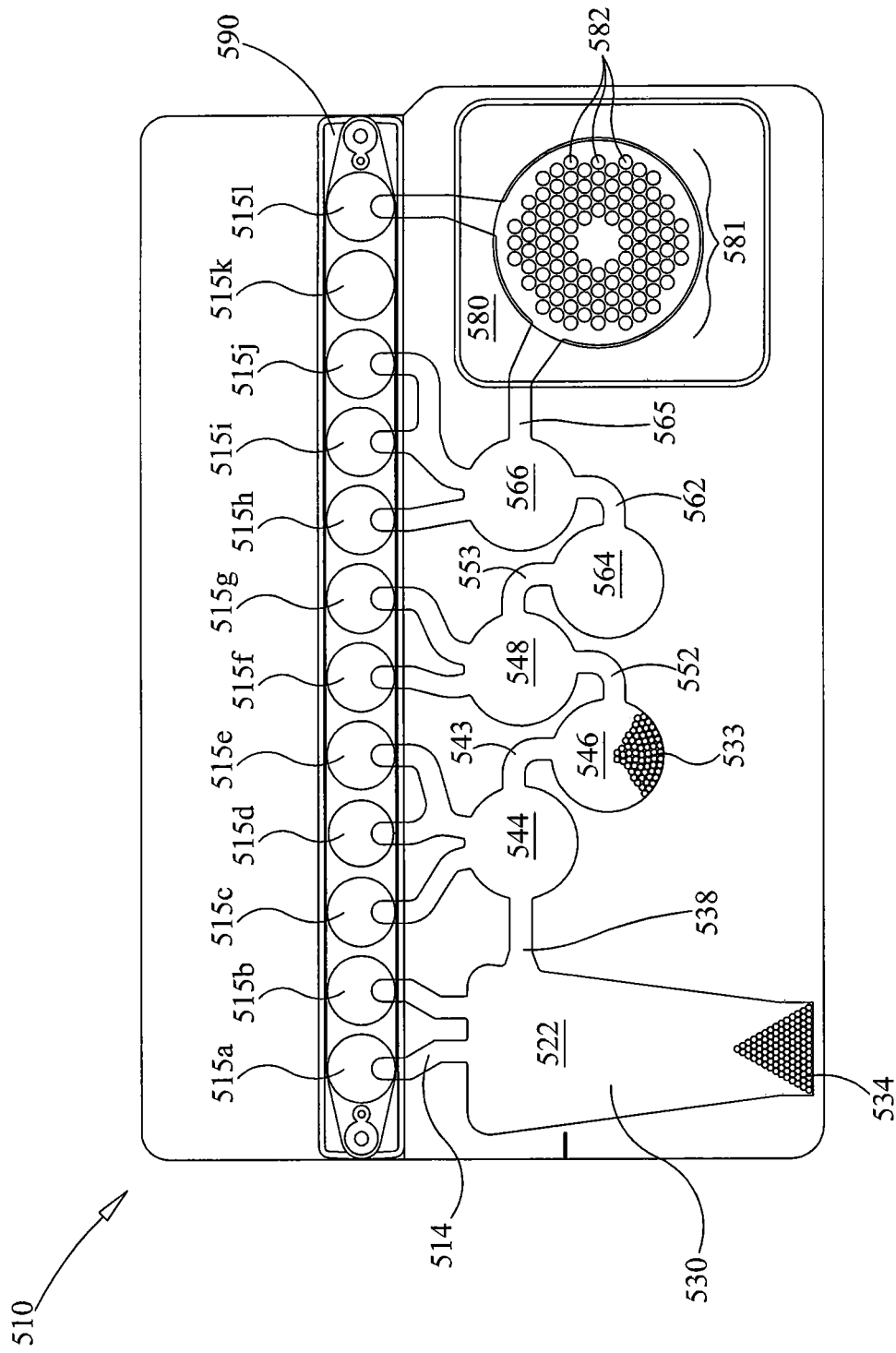
FIG. 1 shows a flexible pouch according to one embodiment of the present invention.

Example embodiments are described below with reference to the accompanying drawings. Many different forms and embodiments are possible without deviating from the spirit and teachings of this disclosure and so the disclosure should not be construed as limited to the example embodiments set forth herein. Rather, these example embodiments are provided so that this disclosure will be thorough and complete, and will convey the scope of the disclosure to those skilled in the art. In the drawings, the sizes and relative sizes of layers and regions may be exaggerated for clarity. Like reference numbers refer to like elements throughout the description.

Unless defined otherwise, all terms (including technical and scientific terms) used herein have the same meaning as commonly understood by one of ordinary skill in the art to which the present disclosure pertains. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. While a number of methods and materials similar or equivalent to those described herein can be used in the practice of the present disclosure, only certain exemplary materials and methods are described herein.

All publications, patent applications, patents or other references mentioned herein are incorporated by reference for in their entirety. In case of a conflict in terminology, the present specification is controlling.

Various aspects of the present disclosure, including devices, systems, methods, etc., may be illustrated with reference to one or more exemplary implementations. As used herein, the terms "exemplary" and "illustrative" mean "serving as an example, instance, or illustration," and should not necessarily be construed as preferred or advantageous over other implementations disclosed herein. In addition, reference to an "implementation" or "embodiment" of the present disclosure or invention includes a specific reference to one or more embodiments thereof, and vice versa, and is intended to provide illustrative examples without limiting the scope of the invention, which is indicated by the appended claims rather than by the following description.

It will be noted that, as used in this specification and the appended claims, the singular forms "a," "an," and "the" include plural referents unless the content clearly dictates otherwise. Thus, for example, reference to "a tile" includes one, two, or more tiles. Similarly, reference to a plurality of referents should be interpreted as comprising a single referent and/or a plurality of referents unless the content and/or context clearly dictate otherwise. Thus, reference to "tiles" does not necessarily require a plurality of such tiles. Instead, it will be appreciated that independent of conjugation; one or more tiles are contemplated herein.

As used throughout this application the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

As used herein, directional and/or arbitrary terms, such as "top," "bottom," "left," "right," "up," "down," "upper," "lower," "inner," "outer," "internal," "external," "interior," "exterior," "proximal," "distal," "forward," "reverse," and the like can be used solely to indicate relative directions and/or orientations and may not be otherwise intended to limit the scope of the disclosure, including the specification, invention, and/or claims.

It will be understood that when an element is referred to as being "coupled," "connected," or "responsive" to, or "on," another element, it can be directly coupled, connected, or responsive to, or on, the other element, or intervening elements may also be present. In contrast, when an element is referred to as being "directly coupled," "directly connected," or "directly responsive" to, or "directly on," another element, there are no intervening elements present.

Example embodiments of the present inventive concepts are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments of the present inventive concepts should not be construed as limited to the particular shapes of regions illustrated herein but are to include deviations in shapes that result, for example, from manufacturing. Accordingly, the regions illustrated in the figures are schematic in nature and their shapes are not intended to illustrate the actual shape of a region of a device and are not intended to limit the scope of example embodiments.

It will be understood that although the terms "first," "second," etc. may be used herein to describe various elements, these elements should not be limited by these terms. These terms are only used to distinguish one element from another. Thus, a "first" element could be termed a "second" element without departing from the teachings of the present embodiments.

It is also understood that various implementations described herein can be utilized in combination with any other implementation described or disclosed, without departing from the scope of the present disclosure. Therefore, products, members, elements, devices, apparatus, systems, methods, processes, compositions, and/or kits according to certain implementations of the present disclosure can include, incorporate, or otherwise comprise properties, features, components, members, elements, steps, and/or the like described in other implementations (including systems, methods, apparatus, and/or the like) disclosed herein without departing from the scope of the present disclosure. Thus, reference to a specific feature in relation to one implementation should not be construed as being limited to applications only within said implementation.

The headings used herein are for organizational purposes only and are not meant to be used to limit the scope of the description or the claims. To facilitate understanding, like reference numerals have been used, where possible, to designate like elements common to the figures. Furthermore, where possible, like numbering of elements have been used in various figures. Furthermore, alternative configurations of a particular element may each include separate letters appended to the element number.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The word "or" as used herein means any one member of a particular list and also includes any combination of members of that list.

By "sample" is meant an animal; a tissue or organ from an animal; a cell (either within a subject, taken directly from a subject, or a cell maintained in culture or from a cultured cell line); a cell lysate (or lysate fraction) or cell extract; a solution containing one or more molecules derived from a cell, cellular material, or viral material (e.g. a polypeptide or nucleic acid); or a solution containing a non-naturally occurring nucleic acid, which is assayed as described herein. A sample may also be any body fluid or excretion (for example, but not limited to, blood, urine, stool, saliva, tears, bile, or cerebrospinal fluid) that may or may not contain host or pathogen cells, cell components, or nucleic acids.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof By "probe," "primer," or "oligonucleotide" is meant a single-stranded nucleic acid molecule of defined sequence that can base-pair to a second nucleic acid molecule that contains a complementary sequence (the "target"). The stability of the resulting hybrid depends upon the length, GC content, and the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes, primers, and oligonucleotides may be detectably-labeled, either radioactively, fluorescently, or non-radioactively, by methods well-known to those skilled in the art. dsDNA binding dyes may be used to detect dsDNA. It is understood that a "primer" is specifically configured to be extended by a polymerase, whereas a "probe" or "oligonucleotide" may or may not be so configured.

By "dsDNA binding dyes" is meant dyes that fluoresce differentially when bound to double-stranded DNA than when bound to single-stranded DNA or free in solution, usually by fluorescing more strongly. While reference is made to dsDNA binding dyes, it is understood that any suitable dye may be used herein, with some non-limiting illustrative dyes described in U.S. Pat. No. 7,387,887, herein incorporated by reference. Other signal producing substances may be used for detecting nucleic acid amplification and melting, illustratively enzymes, antibodies, etc., as are known in the art.

By "specifically hybridizes" is meant that a probe, primer, or oligonucleotide recognizes and physically interacts (that is, base-pairs) with a substantially complementary nucleic acid (for example, a sample nucleic acid) under high stringency conditions, and does not substantially base pair with other nucleic acids.

By "high stringency conditions" is meant typically occur at about melting temperature (Tm) minus 5° C. (i.e. 5° below the Tm of the probe). Functionally, high stringency conditions are used to identify nucleic acid sequences having at least 80% sequence identity.

While PCR is the amplification method used in the examples herein, it is understood that any amplification method that uses a primer may be suitable. Such suitable procedures include polymerase chain reaction (PCR); strand displacement amplification (SDA); nucleic acid sequence-based amplification (NASBA); cascade rolling circle amplification (CRCA), loop-mediated isothermal amplification of DNA (LAMP); isothermal and chimeric primer-initiated amplification of nucleic acids (ICAN); target based-helicase dependent amplification (HDA); transcription-mediated amplification (TMA), and the like. Therefore, when the term PCR is used, it should be understood to include other alternative amplification methods. For amplification methods without discrete cycles, reaction time may be used where measurements are made in cycles or Cp, and additional reaction time may be added where additional PCR cycles are added in the embodiments described herein. It is understood that protocols may need to be adjusted accordingly.

While various examples herein reference human targets and human pathogens, these examples are illustrative only. Methods, kits, and devices described herein may be used to detect and sequence a wide variety of nucleic acid sequences from a wide variety of samples, including, human, veterinary, industrial, and environmental.

Various embodiments disclosed herein use a self-contained nucleic acid analysis pouch to assay a sample for the presence of various biological substances, illustratively antigens and nucleic acid sequences, illustratively in a single closed system. Such systems, including pouches and instruments for use with the pouches, are disclosed in more detail in U.S. Pat. Nos. 8,394,608; and 8,895,295; and U.S. Patent Application No. 2014-0283945, herein incorporated by reference. However, it is understood that such pouches are illustrative only, and the nucleic acid preparation and amplification reactions discussed herein may be performed in any of a variety of open or closed system sample vessels as are known in the art, including 96-well plates, plates of other configurations, arrays, carousels, and the like, using a variety of nucleic acid purification and amplification systems, as are known in the art. While the terms "sample well", "amplification well", "amplification container", or the like are used herein, these terms are meant to encompass wells, tubes, and various other reaction containers, as are used in these amplification systems. In one embodiment, the pouch is used to assay for multiple pathogens. The pouch may include one or more blisters used as sample wells, illustratively in a closed system. Illustratively, various steps may be performed in the optionally disposable pouch, including nucleic acid preparation, primary large volume multiplex PCR, dilution of primary amplification product, and secondary PCR, culminating with optional real-time detection or post-amplification analysis such as melting-curve analysis. Further, it is understood that while the various steps may be performed in pouches of the present invention, one or more of the steps may be omitted for certain uses, and the pouch configuration may be altered accordingly.

FIG. 1 shows an illustrative pouch 510 that may be used in various embodiments, or may be reconfigured for various embodiments. Pouch 510 is similar to FIG. 15 of U.S. Pat. No. 8,895,295, with like items numbered the same. Fitment 590 is provided with entry channels 515a through 515l, which also serve as reagent reservoirs or waste reservoirs. Illustratively, reagents may be freeze dried in fitment 590 and rehydrated prior to use. Blisters 522, 544, 546, 548, 564, and 566, with their respective channels 514, 538, 543, 552, 553, 562, and 565 are similar to blisters of the same number of FIG. 15 of U.S. Pat. No. 8,895,295. Second-stage reaction zone 580 of FIG. 1 is similar to that of U.S. Pat. No. 8,895,295, but the second-stage wells 582 of high density array 581 are arranged in a somewhat different pattern. The more circular pattern of high density array 581 of FIG. 1 eliminates wells in corners and may result in more uniform filling of second-stage wells 582. As shown, the high density array 581 is provided with 102 second-stage wells 582. Pouch 510 is suitable for use in the FilmArray® instrument (BioFire Diagnostics, LLC, Salt Lake City, Utah). However, it is understood that the pouch embodiment is illustrative only.

While other containers may be used, illustratively, pouch 510 is formed of two layers of a flexible plastic film or other flexible material such as polyester, polyethylene terephthalate (PET), polycarbonate, polypropylene, polymethylmethacrylate, and mixtures thereof that can be made by any process known in the art, including extrusion, plasma deposition, and lamination. Metal foils or plastics with aluminum lamination also may be used. Other barrier materials are known in the art that can be sealed together to form the blisters and channels. If plastic film is used, the layers may be bonded together, illustratively by heat sealing. Illustratively, the material has low nucleic acid binding capacity.

For embodiments employing fluorescent monitoring, plastic films that are adequately low in absorbance and auto-fluorescence at the operative wavelengths are preferred. Such material could be identified by testing different plastics, different plasticizers, and composite ratios, as well as different thicknesses of the film. For plastics with aluminum or other foil lamination, the portion of the pouch that is to be read by a fluorescence detection device can be left without the foil. For example, if fluorescence is monitored in second-stage wells 582 of the second-stage reaction zone 580 of pouch 510, then one or both layers at wells 582 would be left without the foil. In the example of PCR, film laminates composed of polyester (Mylar, Dupont, Wilmington Del.) of about 0.0048 inch (0.1219 mm) thick and polypropylene films of 0.001-0.003 inch (0.025-0.076 mm) thick perform well. Illustratively, pouch 510 is made of a clear material capable of transmitting approximately 80%-90% of incident light.

In the illustrative embodiment, the materials are moved between blisters by the application of pressure, illustratively pneumatic pressure, upon the blisters and channels. Accordingly, in embodiments employing pressure, the pouch material illustratively is flexible enough to allow the pressure to have the desired effect. The term "flexible" is herein used to describe a physical characteristic of the material of pouch. The term "flexible" is herein defined as readily deformable by the levels of pressure used herein without cracking, breaking, crazing, or the like. For example, thin plastic sheets, such as Saran™ wrap and Ziploc® bags, as well as thin metal foil, such as aluminum foil, are flexible. However, only certain regions of the blisters and channels need be flexible, even in embodiments employing pneumatic pressure. Further, only one side of the blisters and channels need to be flexible, as long as the blisters and channels are readily deformable. Other regions of the pouch 510 may be made of a rigid material or may be reinforced with a rigid material.

Illustratively, a plastic film is used for pouch 510. A sheet of metal, illustratively aluminum, or other suitable material, may be milled or otherwise cut, to create a die having a pattern of raised surfaces. When fitted into a pneumatic press (illustratively A-5302-PDS, Janesville Tool Inc., Milton Wis.), illustratively regulated at an operating temperature of 195° C., the pneumatic press works like a printing press, melting the sealing surfaces of plastic film only where the die contacts the film. Various components, such as PCR primers (illustratively spotted onto the film and dried), antigen binding substrates, magnetic beads, and zirconium silicate beads may be sealed inside various blisters as the pouch 510 is formed. Reagents for sample processing can be spotted onto the film prior to sealing, either collectively or separately. In one embodiment, nucleotide tri-phosphates (NTPs) are spotted onto the film separately from polymerase and primers, essentially eliminating activity of the polymerase until the reaction is hydrated by an aqueous sample. If the aqueous sample has been heated prior to hydration, this creates the conditions for a true hot-start PCR and reduces or eliminates the need for expensive chemical hot-start components.

Pouch 510 may be used in a manner similar to that described in U.S. Pat. No. 8,895,295. In one illustrative embodiment, a 300 μl mixture comprising the sample to be tested (100 μl) and lysis buffer (200 μl) is injected into an injection port (not shown) in fitment 590 near entry channel 515a, and the sample mixture is drawn into entry channel 515a. Water is also injected into a second injection port (not shown) of the fitment 590 adjacent entry channel 515l, and is distributed via a channel (not shown) provided in fitment 590, thereby hydrating up to eleven different reagents, each of which were previously provided in dry form at entry channels 515b through 515l via. These reagents illustratively may include freeze-dried PCR reagents, DNA extraction reagents, wash solutions, immunoassay reagents, or other chemical entities. Illustratively, the reagents are for nucleic acid extraction, first-stage multiplex PCR, dilution of the multiplex reaction, and preparation of second-stage PCR reagents, as well as control reactions. In the embodiment shown in FIG. 1, all that need be injected is the sample solution in one injection port and water in the other injection port. After injection, the two injection ports may be sealed. For more information on various configurations of pouch 510 and fitment 590, see U.S. Pat. No. 8,895,295, already incorporated by reference.

After injection, the sample is moved from injection channel 515a to lysis blister 522 via channel 514. Lysis blister 522 is provided with beads or particles 534, such as ceramic beads, and is configured for vortexing via impaction using rotating blades or paddles provided within the FilmArray® instrument. Bead-milling, by shaking or vortexing the sample in the presence of lysing particles such as zirconium silicate (ZS) beads 534, is an effective method to form a lysate. It is understood that, as used herein, terms such as "lyse," "lysing," and "lysate" are not limited to rupturing cells, but that such terms include disruption of non-cellular particles, such as viruses.

Figure 2:
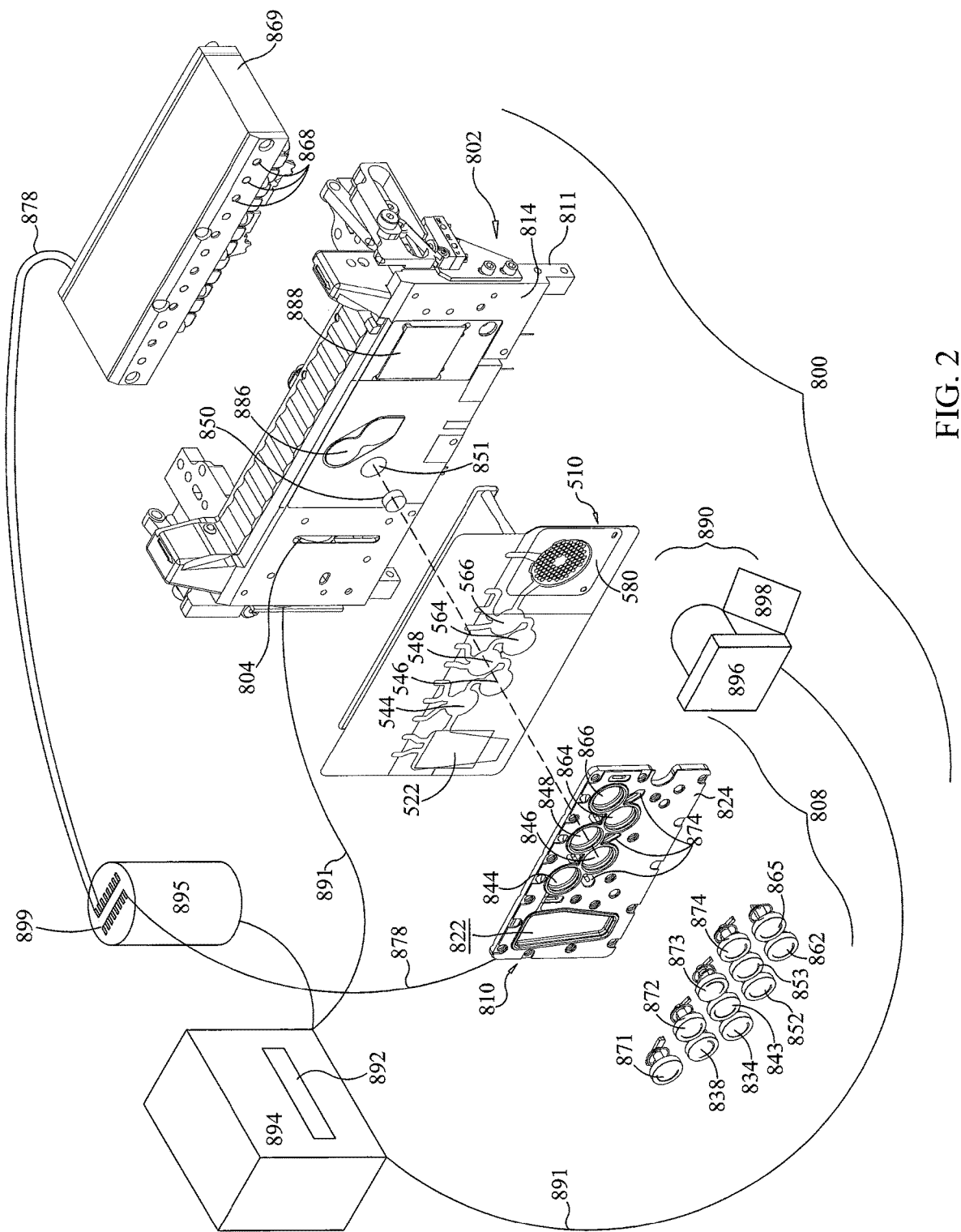
FIG. 2 is an exploded perspective view of an instrument for use with the pouch of FIG. 1, including the pouch of FIG. 1, according to an example embodiment of the present invention.
Figure 4:
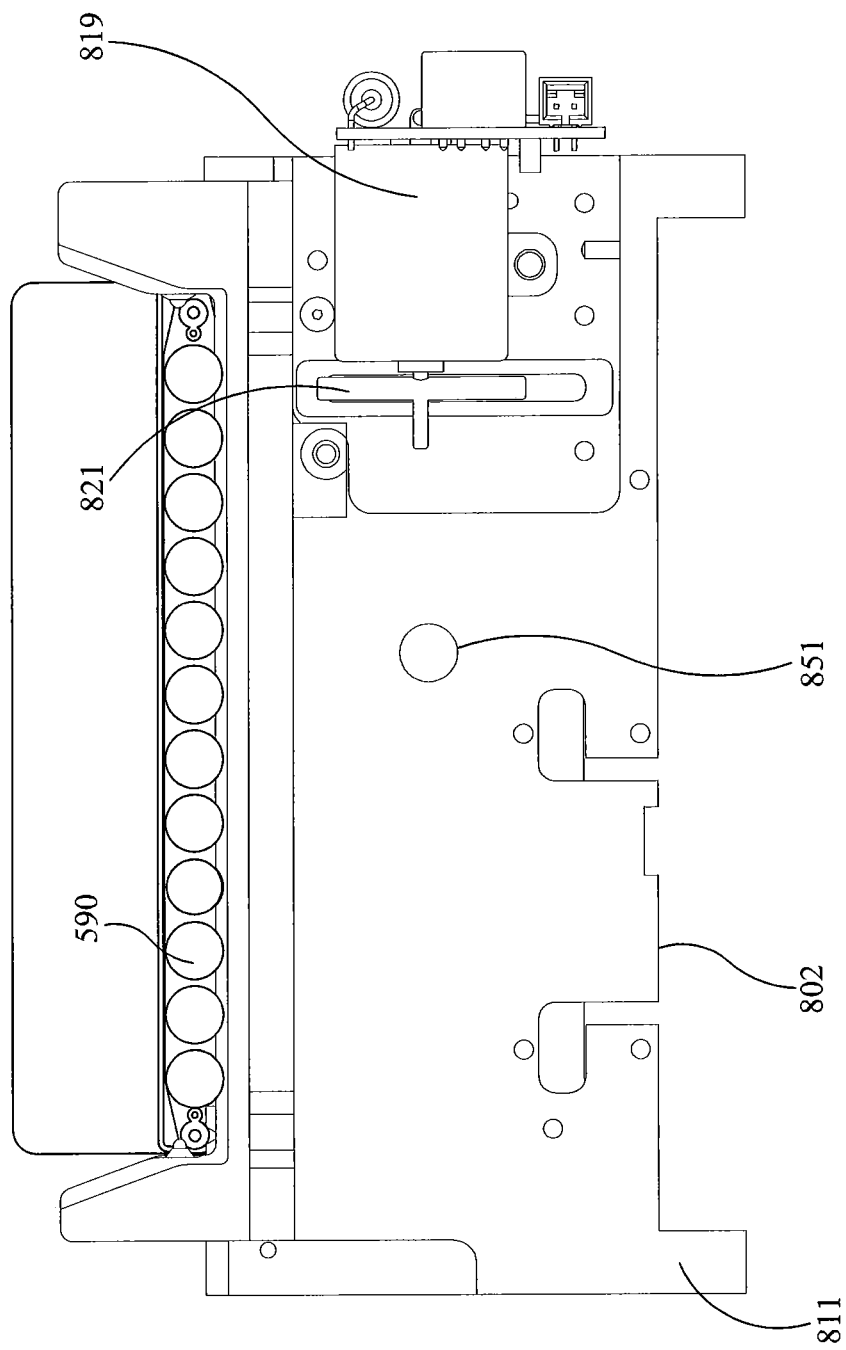
FIG. 4 shows a motor used in one illustrative embodiment of the instrument of FIG. 2.

FIG. 4 shows a bead beating motor 819, comprising blades 821 that may be mounted on a first side 811 of support member 802, of instrument 800 shown in FIG. 2. Blades may extend through slot 804 to contact pouch 510. It is understood, however, that motor 819 may be mounted on other structures of instrument 800. In one illustrative embodiment, motor 819 is a Mabuchi RC-280SA-2865 DC Motor (Chiba, Japan), mounted on support member 802. In one illustrative embodiment, the motor is turned at 5,000 to 25,000 rpm, more illustratively 10,000 to 20,000 rpm, and still more illustratively approximately 15,000 to 18,000 rpm. For the Mabuchi motor, it has been found that 7.2V provides sufficient rpm for lysis. It is understood, however, that the actual speed may be somewhat slower when the blades 821 are impacting pouch 510. Other voltages and speeds may be used for lysis depending on the motor and paddles used. Optionally, controlled small volumes of air may be provided into the bladder 822 adjacent lysis blister 522. It has been found that in some embodiments, partially filling the adjacent bladder with one or more small volumes of air aids in positioning and supporting lysis blister during the lysis process. Alternatively, other structure, illustratively a rigid or compliant gasket or other retaining structure around lysis blister 522, can be used to restrain pouch 510 during lysis. It is also understood that motor 819 is illustrative only, and other devices may be used for milling, shaking, or vortexing the sample.

Once the cells have been adequately lysed, the sample is moved through channel 538, blister 544, and channel 543, to blister 546, where the sample is mixed with a nucleic acid-binding substance, such as silica-coated magnetic beads 533. The mixture is allowed to incubate for an appropriate length of time, illustratively approximately 10 seconds to 10 minutes. A retractable magnet located within the instrument adjacent blister 546 captures the magnetic beads 533 from the solution, forming a pellet against the interior surface of blister 546. The liquid is then moved out of blister 546 and back through blister 544 and into blister 522, which is now used as a waste receptacle. One or more wash buffers from one or more of injection channels 515c to 515e are provided via blister 544 and channel 543 to blister 546. Optionally, the magnet is retracted and the magnetic beads 533 are washed by moving the beads back and forth from blisters 544 and 546 via channel 543. Once the magnetic beads 533 are washed, the magnetic beads 533 are recaptured in blister 546 by activation of the magnet, and the wash solution is then moved to blister 522. This process may be repeated as necessary to wash the lysis buffer and sample debris from the nucleic acid-binding magnetic beads 533, illustratively including 3 or more washes, although one wash may be sufficient for some embodiments disclosed herein and any number of washes is within the scope of this disclosure.

After washing, elution buffer stored at injection channel 515f is moved to blister 548, and the magnet is retracted. The solution is cycled between blisters 546 and 548 via channel 552, breaking up the pellet of magnetic beads 533 in blister 546 and allowing the captured nucleic acids to dissociate from the beads and come into solution. The magnet is once again activated, capturing the magnetic beads 533 in blister 546, and the eluted nucleic acid solution is moved into blister 548.

First-stage PCR master mix from injection channel 515g is mixed with the nucleic acid sample in blister 548. Optionally, the mixture is mixed by forcing the mixture between 548 and 564 via channel 553. After several cycles of mixing, the solution is contained in blister 564, where a pellet of first-stage PCR primers is provided, at least one set of primers for each target, and first-stage multiplex PCR is performed. If RNA targets are present, an RT step may be performed prior to or simultaneously with the first-stage multiplex PCR. First-stage multiplex PCR temperature cycling in the FilmArray® instrument is illustratively performed for 15-20 cycles, although other levels of amplification may be desirable, depending on the requirements of the specific application. The first-stage PCR master mix may be any of various master mixes, as are known in the art. In one illustrative example, the first-stage PCR master mix may be any of the chemistries disclosed in US2015/0118715, herein incorporated by reference, for use with PCR protocols taking 20 seconds or less per cycle.

After first-stage PCR has proceeded for the desired number of cycles, the sample may be diluted, illustratively by forcing most of the sample back into blister 548, leaving only a small amount in blister 564, and adding second-stage PCR master mix from injection channel 515i. Alternatively, a dilution buffer from 515i may be moved to blister 566 then mixed with the amplified sample in blister 564 by moving the fluids back and forth between blisters 564 and 566. If desired, dilution may be repeated several times, using dilution buffer from injection channels 515j and 515k, or injection channel 515k may be reserved for sequencing or for other post-PCR analysis, and then adding second-stage PCR master mix from injection channel 515h to some or all of the diluted amplified sample. It is understood that the level of dilution may be adjusted by altering the number of dilution steps or by altering the percentage of the sample discarded prior to mixing with the dilution buffer or second-stage PCR master mix comprising components for amplification, illustratively a polymerase, dNTPs, and a suitable buffer, although other components may be suitable, particularly for non-PCR amplification methods. If desired, this mixture of the sample and second-stage PCR master mix may be pre-heated in blister 564 prior to movement to second-stage wells 582 for second-stage amplification. Such preheating may obviate the need for a hot-start component (antibody, chemical, or otherwise) in the second-stage PCR mixture.

The illustrative second-stage PCR master mix is incomplete, lacking primer pairs, and each of the 102 second-stage wells 582 is pre-loaded with a specific PCR primer pair. If desired, second-stage PCR master mix may lack other reaction components, and these components may be pre-loaded in the second-stage wells 582 as well. Each primer pair may be similar to or identical to a first-stage PCR primer pair or may be nested within the first-stage primer pair. Movement of the sample from blister 564 to the second-stage wells 582 completes the PCR reaction mixture. Once high density array 581 is filled, the individual second-stage reactions are sealed in their respective second-stage blisters by any number of means, as is known in the art. Illustrative ways of filling and sealing the high density array 581 without cross-contamination are discussed in U.S. Pat. No. 8,895,295, already incorporated by reference. Illustratively, the various reactions in wells 582 of high density array 581 are simultaneously thermal cycled, illustratively with one or more peltier devices, although other means for thermal cycling are known in the art.

In certain embodiments, second-stage PCR master mix contains the dsDNA binding dye LCGreen® Plus (BioFire Diagnostics, LLC) to generate a signal indicative of amplification. However, it is understood that this dye is illustrative only, and that other signals may be used, including other dsDNA binding dyes and probes that are labeled fluorescently, radioactively, chemiluminescently, enzymatically, or the like, as are known in the art. Alternatively, wells 582 of array 581 may be provided without a signal, with results reported through subsequent processing.

Figure 3:
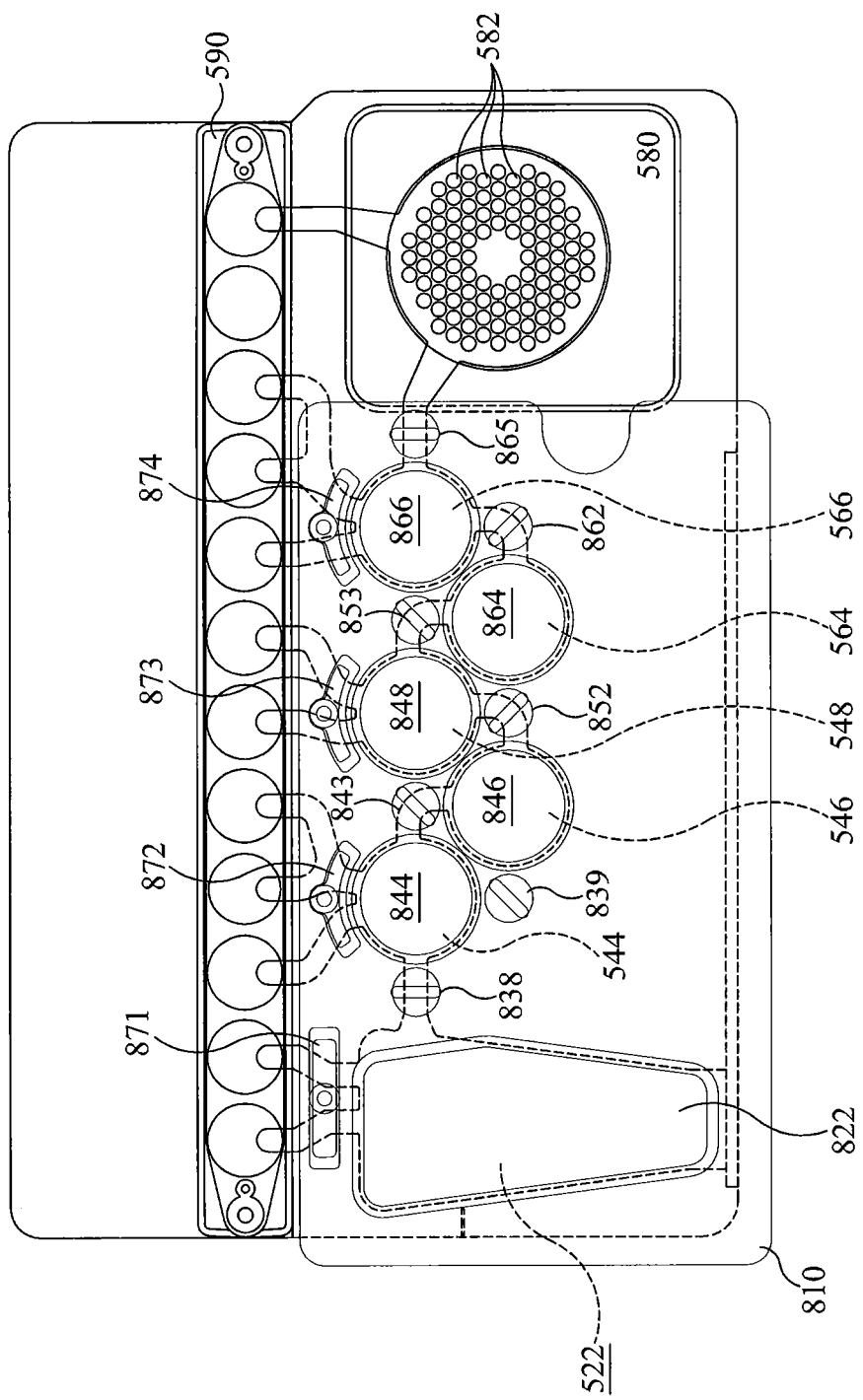
FIG. 3 shows a partial cross-sectional view of the instrument of FIG. 2, including the bladder components of FIG. 2, with the pouch of FIG. 1 shown in dashed lines, according to an example embodiment of the present invention.

When pneumatic pressure is used to move materials within pouch 510, in one embodiment a "bladder" may be employed. The bladder assembly 810, a portion of which is shown in FIGS. 2-3, includes a bladder plate 824 housing a plurality of inflatable bladders 822, 844, 846, 848, 864, and 866, each of which may be individually inflatable, illustratively by a compressed gas source. Because the bladder assembly 810 may be subjected to compressed gas and used multiple times, the bladder assembly 810 may be made from tougher or thicker material than the pouch. Alternatively, bladders 822, 844, 846, 848, 864, and 866 may be formed from a series of plates fastened together with gaskets, seals, valves, and pistons. Other arrangements are within the scope of this invention.

Success of the secondary PCR reactions is dependent upon template generated by the multiplex first-stage reaction. Typically, PCR is performed using DNA of high purity. Methods such as phenol extraction or commercial DNA extraction kits provide DNA of high purity. Samples processed through the pouch 510 may require accommodations be made to compensate for a less pure preparation. PCR may be inhibited by components of biological samples, which is a potential obstacle. Illustratively, hot-start PCR, higher concentration of taq polymerase enzyme, adjustments in $MgCl_2$ concentration, adjustments in primer concentration, and addition of adjuvants (such as DMSO, TMSO, or glycerol) optionally may be used to compensate for lower nucleic acid purity. While purity issues are likely to be more of a concern with first-stage amplification, it is understood that similar adjustments may be provided in the second-stage amplification as well.

When pouch 510 is placed within the instrument 800, the bladder assembly 810 is pressed against one face of the pouch 510, so that if a particular bladder is inflated, the pressure will force the liquid out of the corresponding blister in the pouch 510. In addition to bladders corresponding to many of the blisters of pouch 510, the bladder assembly 810 may have additional pneumatic actuators, such as bladders or pneumatically-driven pistons, corresponding to various channels of pouch 510. FIGS. 2-3 show an illustrative plurality of pistons or hard seals 838, 843, 852, 853, and 865 that correspond to channels 538, 543, 553, and 565 of pouch 510, as well as seals 871, 872, 873, 874 that minimize backflow into fitment 590. When activated, hard seals 838, 843, 852, 853, and 865 form pinch valves to pinch off and close the corresponding channels. To confine liquid within a particular blister of pouch 510, the hard seals are activated over the channels leading to and from the blister, such that the actuators function as pinch valves to pinch the channels shut. Illustratively, to mix two volumes of liquid in different blisters, the pinch valve actuator sealing the connecting channel is activated, and the pneumatic bladders over the blisters are alternately pressurized, forcing the liquid back and forth through the channel connecting the blisters to mix the liquid therein. The pinch valve actuators may be of various shapes and sizes and may be configured to pinch off more than one channel at a time. While pneumatic actuators are discussed herein, it is understood that other ways of providing pressure to the pouch are contemplated, including various electromechanical actuators such as linear stepper motors, motor-driven cams, rigid paddles driven by pneumatic, hydraulic or electromagnetic forces, rollers, rocker-arms, and in some cases, cocked springs. In addition, there are a variety of methods of reversibly or irreversibly closing channels in addition to applying pressure normal to the axis of the channel. These include kinking the bag across the channel, heat-sealing, rolling an actuator, and a variety of physical valves sealed into the channel such as butterfly valves and ball valves. Additionally, small Peltier devices or other temperature regulators may be placed adjacent the channels and set at a temperature sufficient to freeze the fluid, effectively forming a seal. Also, while the design of FIG. 1 is adapted for an automated instrument featuring actuator elements positioned over each of the blisters and channels, it is also contemplated that the actuators could remain stationary, and the pouch 510 could be transitioned in one or two dimensions such that a small number of actuators could be used for several of the processing stations including sample disruption, nucleic-acid capture, first and second-stage PCR, and other applications of the pouch 510 such as immuno-assay and immuno-PCR. Rollers acting on channels and blisters could prove particularly useful in a configuration in which the pouch 510 is translated between stations. Thus, while pneumatic actuators are used in the presently disclosed embodiments, when the term "pneumatic actuator" is used herein, it is understood that other actuators and other ways of providing pressure may be used, depending on the configuration of the pouch and the instrument.

Other prior art instruments teach PCR within a sealed flexible container. See, e.g., U.S. Pat. Nos. 6,645,758 and 6,780,617, and U.S. Patent Application No. 2014/0038272, herein incorporated by reference. However, including the cell lysis within the sealed PCR vessel can improve ease of use and safety, particularly if the sample to be tested may contain a biohazard. In the embodiments illustrated herein, the waste from cell lysis, as well as that from all other steps, remains within the sealed pouch. However, it is understood that the pouch contents could be removed for further testing.

FIG. 2 shows an illustrative instrument 800 that could be used with pouch 510. Instrument 800 includes a support member 802 that could form a wall of a casing or be mounted within a casing. Instrument 800 may also include a second support member (not shown) that is optionally movable with respect to support member 802, to allow insertion and withdrawal of pouch 510. Illustratively, a lid may cover pouch 510 once pouch 510 has been inserted into instrument 800. In another embodiment, both support members may be fixed, with pouch 510 held into place by other mechanical means or by pneumatic pressure.

In the illustrative example, heaters 886 and 888 are mounted on support member 802. However, it is understood that this arrangement is illustrative only and that other arrangements are possible. Bladder plate 810, with bladders 822, 844, 846, 848, 864, 866, hard seals 838, 843, 852, 853, seals 871, 872, 873, 874 form bladder assembly 808 may illustratively be mounted on a moveable support structure that may be moved toward pouch 510, such that the pneumatic actuators are placed in contact with pouch 510. When pouch 510 is inserted into instrument 800 and the movable support member is moved toward support member 802, the various blisters of pouch 510 are in a position adjacent to the various bladders of bladder assembly 810 and the various seals of assembly 808, such that activation of the pneumatic actuators may force liquid from one or more of the blisters of pouch 510 or may form pinch valves with one or more channels of pouch 510. The relationship between the blisters and channels of pouch 510 and the bladders and seals of assembly 808 is illustrated in more detail in FIG. 3.

Each pneumatic actuator is connected to compressed air source 895 via valves 899. While only several hoses 878 are shown in FIG. 2, it is understood that each pneumatic fitting is connected via a hose 878 to the compressed gas source 895. Compressed gas source 895 may be a compressor, or, alternatively, compressed gas source 895 may be a compressed gas cylinder, such as a carbon dioxide cylinder. Compressed gas cylinders are particularly useful if portability is desired. Other sources of compressed gas are within the scope of this invention.

Assembly 808 is illustratively mounted on a movable support member, although it is understood that other configurations are possible.

Several other components of instrument 810 are also connected to compressed gas source 895. A magnet 850, which is mounted on a second side 814 of support member 802, is illustratively deployed and retracted using gas from compressed gas source 895 via hose 878, although other methods of moving magnet 850 are known in the art. Magnet 850 sits in recess 851 in support member 802. It is understood that recess 851 can be a passageway through support member 802, so that magnet 850 can contact blister 546 of pouch 510. However, depending on the material of support member 802, it is understood that recess 851 need not extend all the way through support member 802, as long as when magnet 850 is deployed, magnet 850 is close enough to provide a sufficient magnetic field at blister 546, and when magnet 850 is retracted, magnet 850 does not significantly affect any magnetic beads 533 present in blister 546. While reference is made to retracting magnet 850, it is understood that an electromagnet may be used and the electromagnet may be activated and inactivated by controlling flow of electricity through the electromagnet. Thus, while this specification discusses withdrawing or retracting the magnet, it is understood that these terms are broad enough to incorporate other ways of withdrawing the magnetic field. It is understood that the pneumatic connections may be pneumatic hoses or pneumatic air manifolds, thus reducing the number of hoses or valves required.

The various pneumatic pistons 868 of pneumatic piston array 869 are also connected to compressed gas source 895 via hoses 878. While only two hoses 878 are shown connecting pneumatic pistons 868 to compressed gas source 895, it is understood that each of the pneumatic pistons 868 are connected to compressed gas source 895. Twelve pneumatic pistons 868 are shown.

A pair of heating/cooling devices, illustratively Peltier heaters, are mounted on a second side 814 of support 802. First-stage heater 886 is positioned to heat and cool the contents of blister 564 for first-stage PCR. Second-stage heater 888 is positioned to heat and cool the contents of second-stage blisters 582 of pouch 510, for second-stage PCR. It is understood, however, that these heaters could also be used for other heating purposes, and that other heaters may be included, as appropriate for the particular application.

When fluorescent detection is desired, an optical array 890 may be provided. As shown in FIG. 2, optical array 890 includes a light source 898, illustratively a filtered LED light source, filtered white light, or laser illumination, and a camera 896. Camera 896 illustratively has a plurality of photodetectors each corresponding to a second-stage well 582 in pouch 510. Alternatively, camera 896 may take images that contain all of the second-stage wells 582, and the image may be divided into separate fields corresponding to each of the second-stage wells 582. Depending on the configuration, optical array 890 may be stationary, or optical array 890 may be placed on movers attached to one or more motors and moved to obtain signals from each individual second-stage well 582. It is understood that other arrangements are possible.

As shown, a computer 894 controls valves 899 of compressed air source 895, and thus controls all of the pneumatics of instrument 800. Computer 894 also controls heaters 886 and 888, and optical array 890. Each of these components is connected electrically, illustratively via cables 891, although other physical or wireless connections are within the scope of this invention. It is understood that computer 894 may be housed within instrument 800 or may be external to instrument 800. Further, computer 894 may include built-in circuit boards that control some or all of the components, and may also include an external computer, such as a desktop or laptop PC, to receive and display data from the optical array. An interface, illustratively a keyboard interface, may be provided including keys for inputting information and variables such as temperatures, cycle times, etc. Illustratively, a display 892 is also provided. Display 892 may be an LED, LCD, or other such display, for example.

EXAMPLES

Example 1: High Density PCR

In one example, it is known that standard commercial immunofluorescence assays for the common respiratory viruses can detect seven viruses: adenovirus, PIV1, PIV2, PIV3, RSV, Influenza A, and Influenza B. A more complete panel illustratively would include assays for other viruses including: coronavirus, human metapneumovirus, rhinovirus, and non-HRV enterovirus. For highly variable viruses such as Adenovirus or HRV, it is desirable to use multiple primers to target all of the branches of the virus' lineage (illustratively 4 outer and 4 inner primer sets respectively). For other viruses such as coronavirus, there are 4 distinct lineages (229E, NL63, OC43, HKU1) that do not vary from one season to another, but they have diverged sufficiently enough that separate primer sets are required. The FilmArray® Respiratory Panel (BioFire Diagnostics, LLC of Salt Lake City, Utah) includes Adenovirus, Coronavirus HKU1, Coronavirus NL63, Coronavirus 229E, Coronavirus OC43, Human Metapneumovirus, Human Rhinovirus/Enterovirus, Influenza A, Influenza A/H1, Influenza A/H3, Influenza A/H1-2009, Influenza B, Parainfluenza Virus 1, Parainfluenza Virus 2, Parainfluenza Virus 3, Parainfluenza Virus 4, and Respiratory Syncytial Virus. In addition to these viruses, the FilmArray® Respiratory Panel includes three bacteria: *Bordetella pertussis, Chlamydophila pneumonia*, and *Mycoplasma* pneumonia. The high density array 581 is able to accommodate such a panel in a single pouch 510. Other panels are available for the FilmArray®, each assaying for at least 20 pathogens.

Example 2: Pouch Loading

Figure 5:
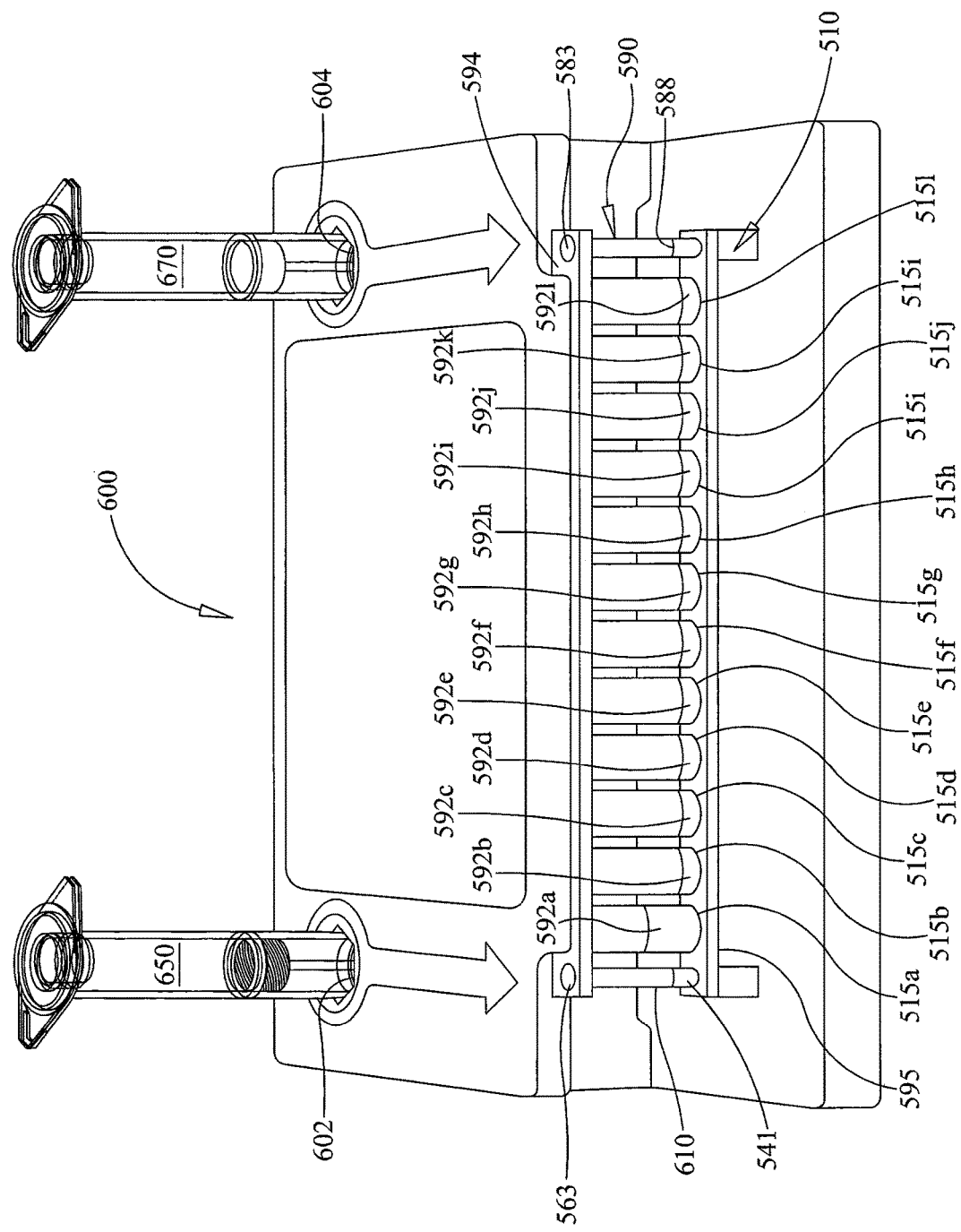
FIG. 5 shows a loading station for loading the pouch of FIG. 1, including the pouch of FIG. 1, according to an example embodiment of the present invention.

FIG. 5 shows a loading station 600. As shown, pouch 510 of FIG. 1 has been loaded into slot 610 of loading station 600, such that only fitment 590 of pouch 510 is visible. As shown, loading station 600 is provided with a sample vial receptacle 602 for holding sample vial 650 and hydration vial receptacle 604 for holding hydration vial 670. However, it is understood that the receptacles and vials are for aiding workflow and are illustrative only. Other configurations and use with other pouches and other devices are within the scope of this disclosure.

A sample is pipetted or otherwise loaded into sample vial 650. As discussed in more detail below, depending on work flow, sample vial 650 may already contain a buffer or other fluid 652 for receiving the biological sample, or the operator may add the biological sample in an appropriate buffer to sample vial 650. Optionally, the buffer may be provided in a separate ampoule, with an appropriate amount of buffer apportioned. Similarly, hydration vial 670 may be preloaded with water, buffer, or other fluid 672, or the operator may load hydration vial 670 with such fluid.

Illustrative fitment 590 includes an injection port 541 illustratively formed near second surface 595 of fitment 590. As shown, injection port 541 is located in sample injection opening 563, which is configured to receive a cannulated transfer vessel through first surface 594 of fitment 590, such as a cannulated syringe. In this illustrative configuration, injection port 541 is protected from accidental puncture and is not opened until a cannulated transfer vessel is placed into sample injection opening 563. Similarly, illustrative fitment 590 includes a second injection port 588 illustratively formed near second surface 595 of fitment 590, and is located in hydration fluid injection opening 583, which is configured similarly to sample injection opening 563. As configured in this illustrative embodiment, injection port 541 is for receiving the sample to be tested, which sample will be moved to chamber 592*a* or directly into lysis blister 522 (FIG. 1), and second injection port 588 is configured for receiving the hydration fluid 672 (displayed in FIG. 7), such as water or buffer, which hydration fluid 672 will be moved to chambers 592*b* through 592*l*, for subsequent movement through entry channels 515*b* through 515*l*. It is understood that the arrangement of injection ports 541 and 588 and openings 563 and 583 is illustrative and that other configurations are within the scope of this disclosure.

Figure 6:
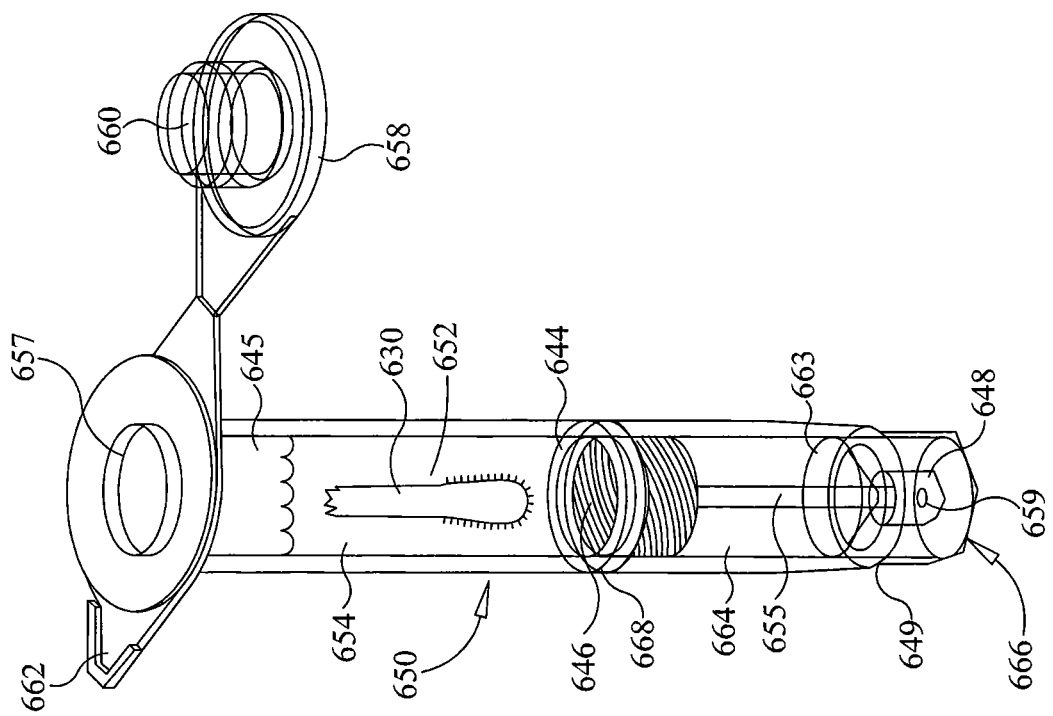
FIG. 6 shows a sample vial for loading a sample into the pouch of FIG. 1.

Illustrative sample vial 650, as best shown in FIG. 6, is comprised of a top surface 662, a vial body 654, and a cannula 655, in an arrangement similar to many cannulated syringes. In this illustrative embodiment, rather than the plunger found in many cannulated syringes, sample vial 650 is provided with a cap 658 for extending through top surface 662 for sealing body 654. Illustratively, the operator would pour, pipette, insert swab, scoop solid or semi-solid material, or otherwise transfer a fluid and/or other materials through opening 657 in top surface 662 and into vial body 654.

Depending on the type of sample to be tested, sample vial 650 may be provided with a filter 646, illustratively located at or near the hexagonal bottom surface 666 of vial body 654. As shown, filter 646 is held in place by o-ring 644. However, it is understood that filter 646 may be held in place by adhesive, by welding, by being press-fit into place, or by other means, as are known in the art. When cannula 655 is inserted into sample injection opening 563 and the sample is drawn into pouch 510, the sample material is filtered as it is pulled through filter 646 and into cannula 655. While the selection of filter material depends on the sample type and particle size, suitable filters for various biological samples include Pall 100 μm Absolute Ultipleat Polypropylene Melt Blown Media and Millipore 80 μm Polypropylene Net Filter. Most syringe filters are designed to exclude organisms of a certain size, thereby removing those organisms from the filtrate. Unlike such pre-existing filters, these illustrative filters were chosen based on their ability to exclude larger particulates found in stool, soil, powder, etc., while allowing target organisms (e.g., bacterial, viral, protozoan and fungal organisms) of approximately 60 µm in diameter or less to pass through in the filter. Also, the illustrative filter material is inert (i.e. does not bind organism or nucleic acid) and is relatively resistant to clogging. It is understood that these illustrative filters were chosen for samples that include protozoans as target organisms (up to about 60 µm). Because some pouch configurations may test only for smaller targets, filters with a smaller pore size may be desired, such as filters with pore sizes of 1-10 µm for bacteria and fungi, and pore sizes of less than 1 µm if only viral particles are to be detected. Of course, the larger pore size filter can still be used to filter smaller targets. Such filters may be particularly useful for sample types that have a large amount of particulate matter, such as soil, stool, and powder that may clog the fluid system. Further, it is understood that the pore size is chosen based on the materials to be filtered, and that other pore sizes are within the scope of this invention.

It is understood that one or more components useful for sample preparation may be provided dried in vial body 654. Such additives may include buffering agents, stabilizers, proteases, DNAses, DNAse inhibitors, RNases, RNase inhibitors, lysozymes, reducing agents, and the like. Alternatively, such components may be included in the sample buffer, or may be added downstream, after the sample has exited vial 650 for further processing. It is understood that the selection of such additives depends on the sample type and on the further processing desired. Additives that help reduce viscosity or aid in solubility, to allow the sample to pass through filter 646 are particularly helpful.

As shown, bottom cap 664 is provided with a hexagonal portion 666, which is configured to fit into the hexagonally shaped sample vial receptacle 602. While hexagonal portion 666 and sample vial receptacle are hexagonal in the illustrative embodiment, it is understood that other shapes may be used, and that the hexagonal or other mating or interlocking shapes may be provided to assist the operator in removing bottom cap 664. Alternatively, the operator may remove bottom cap 664 by other means, such as using two hands to twist bottom cap 664 from vial body 654. Bottom cap 654 may be press-fit on, threaded onto, or otherwise affixed to vial body 654.

In the illustrative embodiment, bottom cap 664 is provided with a seat 648, whereby a bottom end 659 of cannula 655 extends into seat 648. Illustratively, bottom end 659 of cannula 655 fits tightly into seat 648, such that seat 648 provides an airtight seal around the open bottom end 659 of cannula 655. Optionally, vents 649 are provided between bottom cap 664 and vial body 654.

Figure 7:
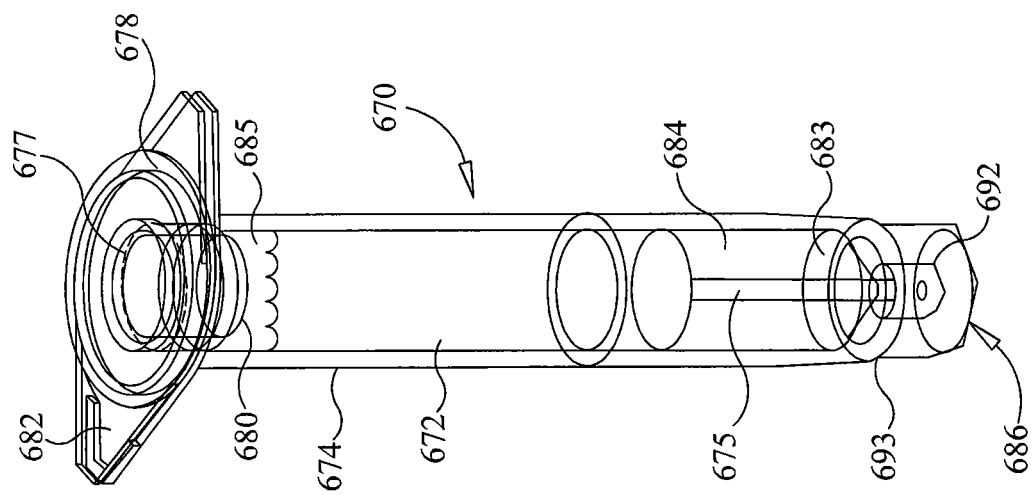
FIG. 7 shows a hydration vial for providing a hydration fluid to the pouch of FIG. 1, according to an example embodiment of the present invention.

Turning now to FIG. 7, hydration vial 670 may be configured similarly to sample vial 650. However, it may be desirable to preload hydration vial 670 with hydration fluid 672 and pre-seal the hydration fluid 672 in hydration vial 670, as shown in FIG. 7. Illustrative hydration vial 670, as shown in FIG. 7, is comprised of a top surface 682, a vial body 674, and a cannula 675, in an arrangement similar to that of sample vial 650. However, tongue 680 of cap 678 of illustrative hydration vial 670 is already press-fit into opening 677 of top surface 682, and cap 678 may be sealed to top surface 682, thereby preventing opening of hydration vial 670. This arrangement is illustrative only, and it is understood that other ways of sealing hydration fluid 672 within hydration vial 670 are envisioned herein. Illustratively, vial body 674 and cannula 675 may be provided completely full or essentially completely full of fluid, so that handling or rotating hydration vial 670 will not permit air to enter cannula 675. Alternatively, some air 685 or other gas may be present within vial body 674, and the operator may maintain hydration body in an upright position to prevent air from entering cannula 675. In yet another alternative embodiment, the air 685 may be provided under pressure, and removal of bottom cap 684 would result in hydration fluid being forced through cannula 675. As shown, hydration vial 670 is not provided with a filter, although one may be provided, if desired.

Bottom cap 684 may be provided to retain any fluid that might drip from cannula 675, as well as preventing contamination of hydration fluid 672 in cannula 675. A wiper 683 may be provided in bottom cap 684 to wipe excess fluid from the bottom of cannula 675. The conical shape of wiper 683 may also aid in retaining drips in bottom cap 684 during subsequent handling and disposal. In the illustrative embodiment, bottom cap 684 is provided with a hexagonal portion 686 for mating with the hexagonally shaped hydration vial receptacle 604, although other shapes are possible, as discussed above, with respect to sample vial 650. Hexagonal portion 686 of hydration vial 670 and hexagonally shaped hydration vial receptacle 604 may be of different dimensions and/or different shapes than hexagonal portion 666 of sample vial 650 and hexagonally shaped sample vial receptacle 602, such that only sample vial 650 will readily fit into sample vial receptacle 602 and only hydration vial 670 will readily fit into hydration vial receptacle 604, to reduce the chance of the operator confusing the sample vial 650 and hydration vial 670, so that the proper fluids are injected through ports 541 and 588. In addition, sample vial 650 and injection opening 563 may be partially or entirely provided in a matching specific color, illustratively red, while hydration vial 67Q and injection opening 583 may be partially or entirely provided in a different matching specific color, illustratively blue, to provide the operator with visual assistance in providing the proper fluids in ports 541 and 588. To further minimize risk of inserting the wrong liquid into the wrong injection opening, the diameter of cannula 655 may differ from the diameter of cannula 675, and the diameters of sample injection opening 563 and hydration fluid injection opening 583 may similarly differ. Other configurations are within the scope of this disclosure.

Returning to FIG. 5, illustratively, to load pouch 510, the operator would place sample vial 650 into sample vial receptacle 602 and hydration vial 670 into hydration vial receptacle 604 on loading station 600. Pouch 510 would also be placed into slot 610. The sample would be placed into the sample buffer 652 in any way suitable for the sample type, including inserting a swab 630, pipetting a fluid sample, dripping blood from a patient directly into the vial body, and placing a solid or semi-solid sample such as stool into the vial body, with optional vortexing or other mixing, as is standard in the art. Depending on the sample type and desired target nucleic acids, the sample buffer may contain one or more additives or stabilizers, illustratively for treating a biological or environmental sample, such as proteases, DNases, DNase inhibitors, RNases, RNase inhibitors, lysozymes, and the like. Additionally or alternatively, these additives may be provided in the pouch 510. Preferably before vortexing or mixing, the operator would close sample vial 650 by placing tongue 660 of cap 658 through opening 657. Inserting tongue 660 pressurizes the air contained within vial body 654. Illustratively, tongue 660 has a volume equal to or greater than the volume of cannula 655.

Illustratively, when bottom cap 664 is removed, the airtight seal between seat 648 bottom end 659 of cannula 655 is broken, and substantially all air is forced out of cannula 655. If the volume of tongue 660 is greater than the volume of cannula 655, such would help ensure that the maximal amount of air is displaced from cannula 655. Any overflow in the amount of fluid forced into and potentially through cannula 655 can be captured in bottom cap 664 and removed from the bottom of cannula 655 by wiper 663. By completely or essentially completely filling cannula 655, the quantity of bubbles in pouch 510 upon loading of the pouch is minimized. One or more vents 649 may aid in separation of bottom cap 664 from hydration vial 650.

Because bottom cap 664 is provided with a hexagonal portion 666, which is configured to fit into the hexagonally shaped sample vial receptacle 602, the operator can easily twist off bottom cap 654 while bottom cap is engaging receptacle 602, thereby exposing cannula 655. Cannula 655 is then inserted into sample injection opening 563 and is pushed in, opening injection port 541. A vacuum inside pouch 590 (or reduced pressure (inside the pouch relative to atmospheric pressure or pressure outside the pouch) illustratively forces the sample through the filter (if present), with or without pressure from the vial body, may be used to draw the sample into pouch 510, illustratively into chamber 592a in fitment 590, for subsequent movement into lysis chamber 522. By assuring that cannula 655 is substantially filled with fluid 652, the amount of air or other gas moved from sample vial 650 into pouch 510 is minimized, thereby minimizing the size and quantity of bubbles. Furthermore, when a prior art syringe with a plunger is used and the vacuum inside pouch 590 draws fluid, the plunger is drawn down the syringe, thereby equilibrating the pressure inside the syringe. In the embodiment of FIGS. 5-6, because the opening at the top of each of the vial bodies is sealed, when the vacuum from inside pouch 590 draws fluid from the vial, the vial will also experience negative pressure and may degas the sample and draw some remaining air bubbles out of the pouch 590. Cannula 655 is then withdrawn from sample injection opening 563 and sample vial 650 and bottom cap 664 are disposed of according to protocols. Since the vial body 654 is under negative pressure, as cannula 655 is withdrawn, air bubbles that may have collected near injection port 541 may be drawn out of pouch 510, further reducing air bubbles in the pouch.

Similarly, the operator twists off bottom cap 684 from hydration vial 670, thereby exposing cannula 675. If the contents of hydration vial 670 are provided under pressure, a small amount of hydration fluid may leak out into bottom cap 684 when cannula 675 is separated from seat 692. One or more vents 693 may aid in separation of bottom cap 684 from hydration vial 670. Cannula 675 is then inserted into hydration injection opening 583 and is pushed in, opening injection port 588. Vacuum from inside fitment 590 may be used to draw the hydration fluid into pouch 510, illustratively into chambers 592b-592l, for subsequent movement into various blisters of pouch 510. Cannula 675 is removed from hydration injection opening 583, pouch 510 is removed from loading station 600 and placed into instrument 800, and the run started. It is understood that removal of the vials is illustrative only. If the configuration of the instrument and vials permit, the vials may be inserted permanently in the injection ports, thereby becoming part of the closed system of the pouch and minimizing contamination from the sample. In such an embodiment, a seal bar may not be needed.

In the illustrative embodiment of sample vial 650 discussed above, tongue 660 has a volume equal to or greater than the volume of cannula 655. In one exemplary embodiment where the pouch 510 has a fill volume of 1 ml, vial body 654 may be provided with 1.5 ml of sample fluid 652 and volume of 1 ml of air 645 above the sample fluid. Thus, the air is 40% of the volume of the vial body 654. However, it is understood that other percentages of air may be used, including 10%, 20%, 30% 50%, 60%, 70%, 80%, and amounts in between. When tongue 660 is inserted through opening 657, the air above the sample fluid is compressed, illustratively by about 50%, but compression in the range of 40-60%, 30-70%, 20-80%, and 10-90% are all possible. It is understood that choice of volume of air and sample fluid depends on size of sample, diameter of cannula, whether removal of the vials prior to running the fluidic reaction is desired, and on a number of other factors. For example, scooped or swabbed samples may need a significantly larger volume of sample fluid, regardless of the fill volume of the fluidic system.

Illustrative vial bodies 654 and 674 are cylindrical. However, since these illustrative vials are provided without plungers, it is understood that the vial bodies need not have circular cross-sections, and that any body shape is within the scope of this invention.

Figure 8:
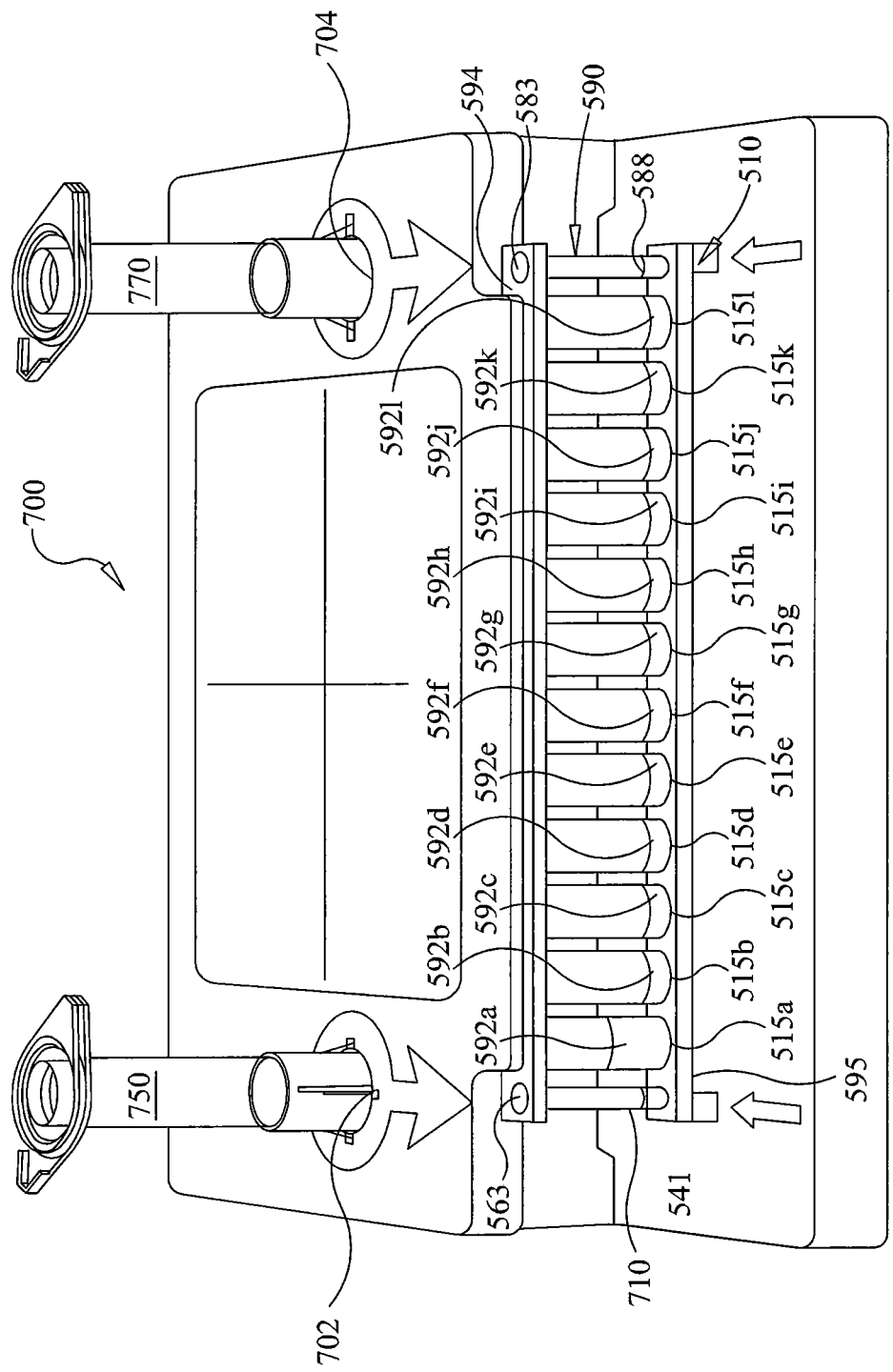
FIG. 8 shows a loading station comparable to FIG. 5, but displaying a different loading station configuration and vials for use with the loading station, according to an example embodiment of the present invention.
Figure 10:
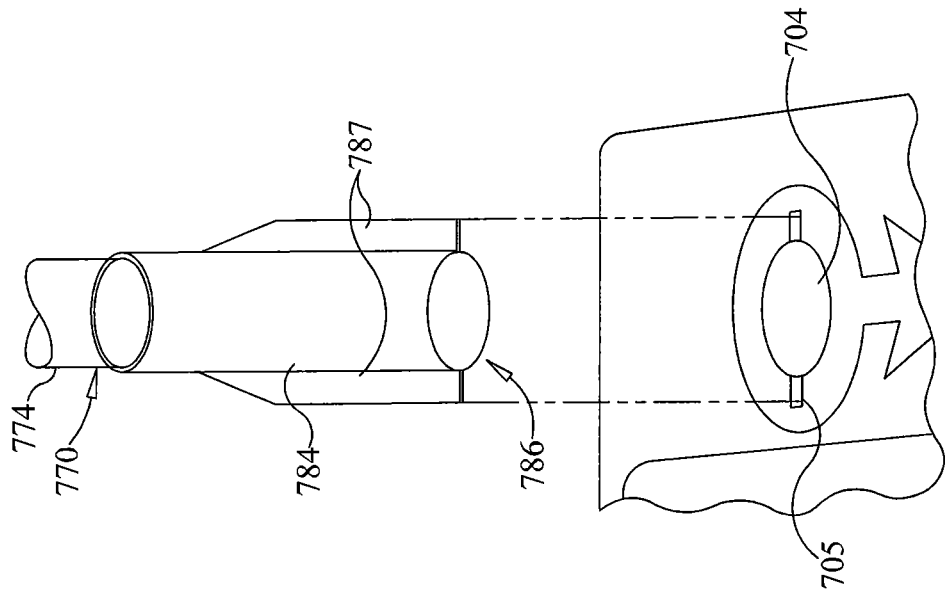
FIG. 10 shows a portion of a hydration vial of FIG. 8 and how the hydration vial keys to the hydration vial receptacle of loading station of FIG. 8, according to an example embodiment of the present invention.
Figure 9:
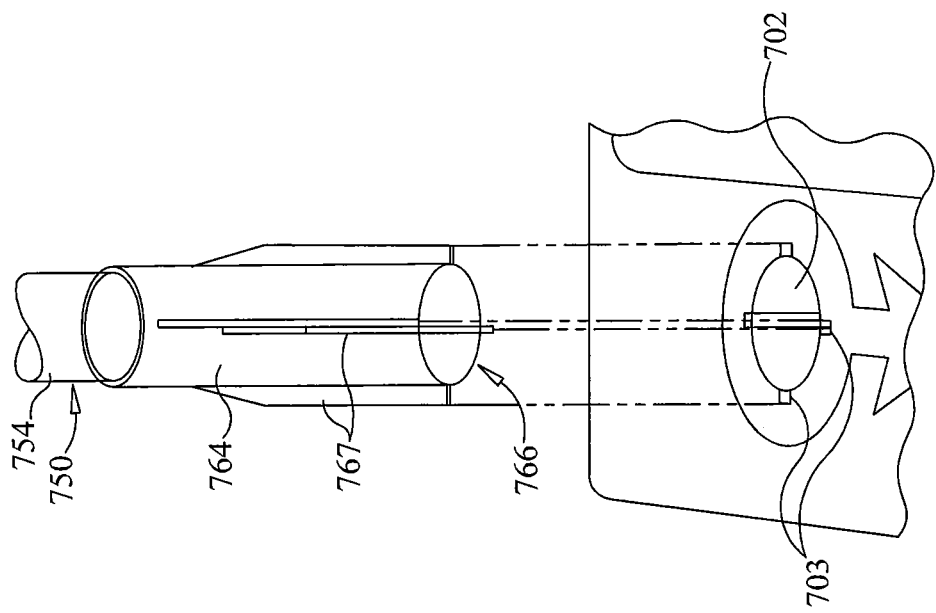
FIG. 9 shows a portion of the sample vial of FIG. 8 and how the sample vial keys to the sample vial receptacle of loading station of FIG. 8, according to an example embodiment of the present invention.

FIGS. 8-10 show an alternative embodiment to loading station 600 and vials 650, 670, with like numbers indicating similar parts. Loading station 700, as shown in FIG. 8, may be similar to loading station 600, with sample vial receptacle 702 and hydration vial receptacle 704, and slot 710 for receiving pouch 510, similar to those shown in FIG. 1. However, according to at least one embodiment, the shape and location of the receptacles are significantly different between loading station 600 and loading station 700. For instance, in at least one embodiment, as compared to receptacles 602, 604 of loading station 600, receptacles 702 and 704 are closer to pouch 510. With this reduced distance, there is less opportunity for drips to occur upon loading pouch 510. Furthermore, as best seen in FIGS. 9-10, bottom cap 764 of sample vial 750 is provided with four relatively short fins 767 that fit within four matching slots 703 of sample vial receptacle 702, and bottom cap 784 of hydration vial 770 is provided with two relatively longer fins 787 that fit within two matching slots 705 of hydration vial receptacle 704. These fins replace the hexagonal portions 666 and 686 of vials 650 and 670, respectively. The larger number of fins 767 on bottom cap 764 prevents sample vial 750 from being placed in hydration vial receptacle 704, and the longer fins 787 of bottom cap 784 prevents hydration vial 770 from being placed in sample vial receptacle 702. However, it is understood that the use of fins of different sizes and numbers is illustrative only, and that different keying systems are within the scope of this disclosure. As discussed above with respect to loading station 600, the receptacles 702, 704 of loading station 700 may be used to assist with twisting off bottom caps 764, 784 from their respective vial bodies 754, 774, to aid with the loading process.

While sample vials 650, 750 and hydration vials 670, 770 are used in the illustrative example for loading of pouch 510, it is understood that these loading vials are suitable for loading any of the pouches disclosed herein. They are also suitable for loading other fluidic or microfluidic device, especially fluidic devices that are configured to draw liquid into the fluidic device using vacuum or suction.

Example 3: Sample Preparation

In this illustrative embodiment, samples from lower respiratory tract infections (LRTI) are used. However, it is understood that the present methods may be suitable for other sample types, including but not limited to difficult-to-process biological and environmental sample types, and is particularly useful for any sample type that is selectively bound and then released from the collection material. LRTIs are common ailments, but identification of the etiological agent can be difficult as a result of biased diagnostic techniques and inhibitory specimen characteristics. The current "Gold Standard" for pathogen identification is bacterial culture, which is highly subjective, lacks sensitivity, and is an incomplete screening method, as culture is only capable of identifying culturable pathogens, whereas non-culturable pathogens go undetected. LRTI specimens include multiple specimen types such as broncho-alveolar lavage (BAL), mini-BAL, bronchial washings, sputum, and endotracheal aspirates (ETAs), all of which have unique and often challenging characteristics. Sputum and ETA specimens can be difficult to manipulate, can be slow to process, and may be highly inhibitory toward molecular detection methods. Additionally, LRTI pathogens include gram-positive and gram-negative bacteria, viruses, and fungal organisms, often requiring a variety of sample processing methods.

Sputum is a semi-solid sample matrix, with variable viscosity and particulates. BALs can have a viscosity similar to clean saline or can have a viscosity similar to sputum, both of which can present processing challenges. Difficulties include un-pipetable specimens, inaccurate pipetting volumes due to variable viscosity, air pockets, pull-back, remnants, and foaming during pouch injection or sample manipulation. With the high viscosity, it can be difficult to isolate pathogens from the sample matrix. In addition, RNase activity found in such samples can affect RNA detection. With such sample types, a combination of physical and chemical lysis can be effective.

The sputum sample may be obtained using any suitable means, including having the patient expectorate into a suitable collection vessel or inducing the patient to produce a specimen. Most pathogen detection methods use a volume transfer system that can be difficult to use with sputum or other viscous samples. Typically, the sample is pre-treated to liquidize the sample for subsequent pipetting. In one illustrative embodiment, swabs are used to transfer sample, reducing or eliminated the need for a pre-treatment step. While pipets, other swabs, and other transfer devices may be used for transfer of the sample, use of flocked swab provides a simple and easy method to introduce a specimen into the testing system while minimizing issues with specimen manipulation. One suitable swab is FLOQSwabs™ (Copan Diagnostics, Murrieta, Calif.). This illustrative flocked swab is hydrophilic and is well suited to collect pathogens. For such viscous samples, illustratively having a viscosity of 3 cP or greater, or solid or semi-solid samples, the flocked swab may preferentially collect organism over solid material. The flocked swab may also preferentially release organism over sample matrix material. Other materials that preferentially collect and release organism over sample matrix may be used to transfer the sample and it is understood that a swab format is illustrative only.

In one illustrative embodiment, the swab 630 may be placed into the sample collected from the patient or may be placed into an environmental sample. The swab 630 then may be placed directly into sample buffer 652 in sample vial 650. Sample buffer 652 may be any buffer, depending on the sample type. As shown in FIG. 6, if desired, the tip of the swab 630 may be broken off and cap 658 may be used to close vial body 654. The presence of the swab tip 630 within vial body 654 should not significantly affect the use of vial 650. Vial 650 may be shaken, illustratively by inverting three times, or shaken more vigorously illustratively for 10 seconds, to release any pathogens that are present from the swab 630. Alternatively, swab 630 may be swirled in the sample buffer 652 and then swab 630 may be removed from vial 650. While not being bound to theory, it is believed that flocked swabs can preferentially collect cells, organisms, and viruses over sample matrices, and then may retain a portion of the sample matrices such as viscous sputum material while at least releasing organisms and viruses. However, it is understood that other swabs or transfer devices may be used in various embodiments. Illustratively, any transfer material that selectively collects and releases the desired sample over the sample matrix can be used to concentrate the sample. Such materials include swabs, brushes, sponges, filters, utensils, loops, paper, or other adsorbent material that selectively binds and releases the desired sample and can be placed in contact with the sample during transfer of the sample for analysis.

Thus, it has been found that such a flocked swab is suitable for both collection and release of pathogens in viscous samples such as LRTI samples, and the flocked swab provides a fairly uniform collection volume. A single FLOQSwabs™ swab collects approximately 150 to 300 µl of sample, including higher viscosity sample types such as sputum, in a fairly reproducible manner. Other materials that reproducibly collect viscous samples with a small sample volume range, illustratively a two-fold to four-fold volume range, are within the scope of the invention. It is understood that a sample volume range is the range of volumes that a sample collection material reproducibly collects, such that an illustrative two-fold range is 150 to 300 µl and an illustrative four-fold range is 150 to 600 µl, although other ranges, including other two-fold and four-fold ranges are within the scope of the invention. Illustrative examples include swabs that are sized to collect 50 to 150 µl, as well as 300 to 1000 µl of sample, and possibly 5 to 10 ml, although it is understood that these ranges are illustrative and that other size ranges are possible. While such swabs may be used to collect specimens from a patient, in one illustrative embodiment, the swab is used collect the specimen in a reproducible manner and to transfer the sample from a suitable collection vessel to another vessel for further processing. However, it is understood that other suitable collection and transfer materials may be used with various embodiments disclosed herein, as are known in the art.

It is known in the art to pretreat difficult samples for a period of time. For example, sputum may be treated with dithiothreitol (DTT) and/or heat for 15 minutes or more, sometimes 30 minutes or more. A sample buffer 652 may be used that may partially or completely liquefy sputum-like specimens, illustratively without such a pretreatment. Buffers known in the art often use detergents at amounts of 10% or less by volume. An illustrative sample buffer 652 according to the present invention may contain 10% or more detergent, illustratively 12%, 15%, 18%, 20% or more detergent. Suitable detergents include non-ionic, ionic and zwitterionic detergents may be used. In one illustrative embodiment, a non-ionic detergent such as 15% Triton-X may be used. Other non-limiting detergents include Tween-20, SDS, and NP-40. It has been found that this higher concentration of detergent may reduce or eliminate the need for a pretreatment such as heating the sample or a DTT mixture pretreatment, prior to nucleic acid extraction. Thus, the sample may be processed with only 5 minutes or less, 2 minutes or less, one minute or less, or even without a hold time. However, it is understood that a pretreatment may be desirable with some sample types. The sample buffer 652 may also contain a guanidinium compound, such as guanidine hydrochloride. In one illustrative example, the buffer is acidic, illustratively with a pH from about 2 to about 6. In certain sample preparation methods, illustratively when the sample type is blood or a blood component, an alcohol such as isopropanol is used in the sample buffer 652. However, other sample buffers may be alcohol-free. It has been found that in various illustrative embodiments employing detergents at a concentration of 10% or more, illustratively 15%, the alcohol may be omitted from the sample buffer 652.

As discussed above, sample vial 650 may be provided with filter 646. When cannula 655 is inserted into sample injection opening 653 and the sample is drawn into pouch 510, the sample material is filtered as it is pulled through filter 646 and into cannula 655. Such a filter 646 may clog with viscous samples such as sputum. In some embodiments, sample vial 650 may be provided with a protease, such as Proteinase K, or the protease may be otherwise provided in sample vial 650 or may be added along with sample buffer 652. If the protease is provided in dried form, introduction of sample buffer 652 rehydrates the protease, and introduction of the sample into sample buffer 652 allows the protease to begin to break down the proteins in the sample, even before the sample is transferred into pouch 510 and reaches lysis blister 522. Action of the protease may aid in reducing the viscosity of the sample, thereby improving the sample's ability to pass through filter 646, or improve other downstream processing steps. Thus, more of the pathogens may be liberated from the sample with protease present in the sample vial 650. However, in some embodiments using a protease, it may be desirable to add the protease into the sample buffer directly or add the protease later in the process, illustratively by having it dried in entry channel 515b, while in other embodiments, the protease may be omitted.

It is understood that preferentially transferring the pathogens by using a flocked swab, higher detergent concentration, filtering through a filter 646 in the presence of a protease, or a combination thereof may obviate the need for a heat or DTT pre-treatment and may break up such viscous samples sufficiently. Such samples may then be ready for a subsequent lysis step, followed by PCR or other testing.

While the above illustrative description focuses on sputum and other LRTI sample types, it is understood that the above methods and devices may be used with a wide variety of sample types, particularly, but not limited to, difficult sample types. In addition to sputum, BAL, and other LRTI sample types, other difficult biological samples include but are not limited to mucus, stool, tissue, tissue homogenate, ground tissue, paraffin treated formalin embedded tissue, bone, bone homogenate, eschars, puss, synovial fluid, lymph node aspirates, and stomach washings. Environmental samples, illustratively soil, surfaces, powders or food, may also present challenges. Transferring using a flocked swab or other transfer means that preferentially collect and release pathogens allows for relatively consistent collection of the pathogens, even from samples that are difficult to pipet or measure accurately. A sample buffer that partially or completely liquefies the sample matrix may be used. Drawing the sample through a filter, illustratively in the presence of higher concentrations of detergent or additives to aid in sample preparation, helps to break up the sample matrix to provide a sample in a format suitable for further processing.

Example 4: Direct Blood Samples

In this embodiment direct blood samples are used for host RNA analysis. As used herein, "direct blood" means blood samples that have not been cultured. Illustrative direct blood samples include whole blood direct from a host organism, illustratively a human, a whole blood fraction (e.g. plasma, or serum), whole blood collected in an anticoagulant solution (e.g. EDTA, Citrate), or whole blood collected in a RNA stabilizing solution. It is understood that host response to infectious, acute, and/or chronic diseases results in changes in production of certain RNA molecules, including but not limited to ribosomal RNA, messenger RNA (mRNA), long noncoding RNA, or small interfering RNA. Such changes in RNA production may be used to indicate the source of the host's illness. The RNA in a direct blood sample is generally purified with automated or manual extraction methods comprised of centrifugation, washing, addition of optimized buffers, protein and nucleic acid digests, often with additional washing, and elution. In many prior art methods, this is all completed using equipment separate from the end point molecular diagnostic tool and often requires 90 minutes or more. The resultant purified samples are then manually added to an end point molecular diagnostic system such as a cDNA microarray or a qPCR instrument. The process for purifying host RNA samples often requires significant time, external equipment, and sample manipulation, all of which can influence sample integrity and quality. An alternative approach is to add the direct blood sample (illustratively in any of the forms defined above) directly to a sample buffer 652. An illustrative sample buffer contains a chaotropic agent that assists in the binding and recovery of nucleic acids, while reducing proteins like RNAses that can degrade RNA. Illustratively, the ratio of direct blood sample to sample buffer is in a range from 1 to 8 to 1 to 1, more specifically in a range from 1 to 5 to 1 to 1.67, although it is understood that other ratios are possible. This sample may then be loaded directly into pouch 510, as discussed above. Host RNA is extracted and purified within the closed system, as discussed above, illustratively with only minimal mixing in vial 650 or without any additional user manipulation. Such sample prep can be completed without any or all of steps involving centrifugation, ethanol precipitation, and DNA digestion. Thus, the sample may be processed with only 2 minutes or less and require no external equipment from the end point molecular diagnostic tool.

An example of this application is the detection of host RNA changes in response to an influenza infection. One-hundred microliters of (100 µL) whole blood sample collected in a RNA stabilizing solution according to manufacturer instructions was added to sample buffer 652, illustratively the sample buffer provided with the FilmArray Respiratory Panel (BioFire Diagnostics, LLC). Illustratively, 300 to 900 µl, or 2-5 fold the volume of the sample of sample buffer may be used. This mixture was then injected into a disposable pouch 510. Sample extraction, purification, reverse-transcription, and two stage of polymerase chain reaction resulted in measurements of significantly upregulated host RNA in response to viral infection relative to a healthy control. The entire process of sample purification and qPCR analysis took less than 70 minutes.

A further example of this application is the detection of host RNA from whole blood collected in an anticoagulant solution (EDTA). One-hundred microliters of (100 µL) this whole blood sample was added to 800 µL of the same sample buffer. This mixture was then injected into a pouch 510. Sample extraction, purification, reverse-transcription, and two stages of polymerase chain reaction resulted in measurements host RNA. The entire process of sample purification and qPCR analysis took less than 70 minutes.

These examples demonstrate that nucleic acids, illustratively high copy number nucleic acids including but not limited to various RNA molecules, bacteria, viruses, or other microorganisms, may be extracted from direct blood samples using only lysis, illustratively chemical and/or mechanical lysis, and nucleic acid purification, illustratively by binding to and eluting from a silica substrate, illustratively no more than 5 washes, or no more than 3 washes, but as few as one wash is within the scope of this invention. These nucleic acids may be extracted and prepared without centrifugation or enzymatic digestion, and without many repeated washing steps. Also as demonstrated, these extracted nucleic acids are suitable as template for subsequent amplification.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached invention disclosure for purposes of illustrating the invention, it will be apparent to those skilled in the art that various changes in the methods and apparatus disclosed herein may be made without departing from the scope of the invention, which is defined in the appended claims. All changes which come within the meaning and range of equivalency of the claims are to be embraced within their scope.

What is claimed is:

1. A sample collection method comprising:
   collecting a sample comprising a biological or environmental substance to provide a collected sample,
   contacting the collected sample with a swab,
   placing the swab with the collected sample in a sample buffer, thereby transferring at least a portion of the collected sample into the sample buffer to provide a sample buffer comprising collected sample, and
   filtering the sample buffer comprising collected sample to provide a sample filtrate,
   wherein, prior to providing the sample filtrate, the method is devoid of a pretreatment step lasting for more than 2 minutes,
   wherein the collecting step is devoid of a swab collection step, and
   wherein the collecting step comprises obtaining the sample from a broncho-alveolar lavage (BAL), mini-BAL, bronchial washing, endotracheal aspirate (ETA), or expectorate to provide the collected sample.

2. The sample collection method of claim 1 further comprising contacting the collected sample in the sample buffer with a protease.

3. The sample collection method of claim 1 wherein the swab is a flocked swab.

4. The sample collection method of claim 1 wherein the collecting step comprises collecting the sample from a sample vessel without pipetting, and wherein the swab is configured to absorb and release an amount of the collected sample within a four-fold volume range.

5. The sample collection method of claim 4 wherein the substance is a viscous substance that has a viscosity of 3 cP or greater.

6. The sample collection method of claim 1 wherein the sample buffer comprises a detergent in an amount of at least 10% by volume of the sample buffer.

7. The sample collection method of claim 1 wherein the sample buffer comprises 15% Triton-X by volume of sample buffer.

8. The sample collection method of claim 1 wherein the filtering step comprises drawing the sample buffer comprising collected sample through a filter in the presence of a protease.

9. The sample collection method of claim 1 wherein the sample comprises a sample matrix and a pathogen, wherein the swab preferentially retains the sample matrix while preferentially releasing the pathogen into the sample buffer.

10. The sample collection method of claim 1 wherein there is no hold time for a pretreatment step.

11. The sample collection method of claim 10 wherein the sample is sputum and the sputum is not heat treated or treated with DTT prior to the placing step.

12. The sample collection method of claim 4 wherein the swab is configured to absorb and release the collected sample from the biological or environmental substance within a two-fold volume range.

13. The sample collection method of claim 5 wherein the viscous substance is sputum.

14. The sample collection method of claim 1 wherein the sample buffer comprises a detergent in an amount of at least 12% by volume of the sample buffer.

15. The sample collection method of claim 1 wherein the sample buffer comprises a detergent in an amount in a range of 12% to 18% by volume of the sample buffer.

16. The sample collection method of claim 1 wherein the sample buffer comprises an alcohol.

17. The sample collection method of claim 1 wherein the sample buffer does not comprise an alcohol.

18. The sample collection method of claim 1 wherein the swab is hydrophilic.

19. A sample collection method comprising:
    collecting a sample comprising a biological or environmental substance to provide a collected sample,
    contacting the collected sample with a swab,
    placing the swab with the collected sample in a sample buffer comprising a detergent in an amount of at least 10% by volume of the sample buffer, thereby transferring at least a portion of the collected sample into the sample buffer to provide a sample buffer comprising collected sample, and
    filtering the sample buffer comprising collected sample to provide a sample filtrate,
    wherein, prior to providing the sample filtrate, the method is devoid of a pretreatment step lasting for more than 2 minutes,
    wherein the collecting step is devoid of a swab collection step, and
    wherein the collecting step comprises obtaining the sample from a broncho-alveolar lavage (BAL), mini-BAL, bronchial washing, endotracheal aspirate (ETA), or expectorate to provide the collected sample.

20. A sample collection method comprising:
    collecting a sample comprising a biological or environmental substance to provide a collected sample,
    contacting the collected sample directly with a swab,
    placing the swab with the collected sample in a sample buffer comprising a detergent in an amount of at least 10% by volume of the sample buffer, thereby transferring at least a portion of the collected sample into the sample buffer to provide a sample buffer comprising collected sample, and
    filtering the sample buffer comprising collected sample to provide a sample filtrate, wherein, prior to providing the sample filtrate, the method is devoid of a pretreatment step lasting for more than 2 minutes, wherein the collecting step is devoid of a swab collection step, wherein the collecting step comprises obtaining the sample from a broncho-alveolar lavage (BAL), mini-BAL, bronchial washing, endotracheal aspirate (ETA), or expectorate to provide the collected sample, and wherein the biological or environmental substance is a viscous substance that has a viscosity of 3 cP or greater.

21. The method of claim 1, wherein the sample is processed to the sample filtrate in 2 minutes or less.

* * * * *

UNITED STATES PATENT AND TRADEMARK OFFICE
CERTIFICATE OF CORRECTION

| | |
|---|---|
| PATENT NO. | : 11,175,205 B2 |
| APPLICATION NO. | : 15/340612 |
| DATED | : November 16, 2021 |
| INVENTOR(S) | : Thatcher et al. |

It is certified that error appears in the above-identified patent and that said Letters Patent is hereby corrected as shown below:

On the Title Page

(56) References Cited, OTHER PUBLICATIONS, Column 2:
Please correct "Panpradistetal." to read -- Panpradist et al. --

In the Specification

Column 8, Line 20:
Please correct "5151" to read -- 515*l* --

Column 18, Line 36:
Please correct "67Q" to read -- 670 --

Signed and Sealed this
Nineteenth Day of July, 2022

*Katherine Kelly Vidal*

Katherine Kelly Vidal
*Director of the United States Patent and Trademark Office*